US008049503B2

(12) United States Patent
Kimura et al.

(10) Patent No.: US 8,049,503 B2
(45) Date of Patent: Nov. 1, 2011

(54) POSITION DETECTING SYSTEM AND POSITION DETECTING METHOD

(75) Inventors: Atsushi Kimura, Akiruno (JP); Atsushi Chiba, Hachioji (JP); Ryoji Sato, Fuchu (JP); Hironao Kawano, Tokyo (JP)

(73) Assignee: Olympus Medical Systems Corp., Tokyo (JP)

( * ) Notice: Subject to any disclaimer, the term of this patent is extended or adjusted under 35 U.S.C. 154(b) by 0 days.

(21) Appl. No.: 12/825,903

(22) Filed: Jun. 29, 2010

(65) Prior Publication Data
US 2011/0012594 A1    Jan. 20, 2011

Related U.S. Application Data

(63) Continuation of application No. PCT/JP2009/069446, filed on Nov. 16, 2009.

(30) Foreign Application Priority Data

Nov. 21, 2008 (JP) ................................. 2008-298591

(51) Int. Cl.
*G01V 3/00* (2006.01)
(52) U.S. Cl. ....................................... 324/319; 324/318
(58) Field of Classification Search .......... 324/300–322; 600/407–445
See application file for complete search history.

(56) References Cited

U.S. PATENT DOCUMENTS

| 4,267,620 | A  | * | 5/1981 | Allen, Jr. .................. 19/239 |
| 6,796,943 | B2 | * | 9/2004 | Mochizuki .................. 600/437 |
| 7,295,007 | B2 | * | 11/2007 | Dold ........................... 324/307 |
| 7,355,409 | B2 | * | 4/2008 | Larsen ........................ 324/326 |
| 7,659,720 | B2 | * | 2/2010 | Furudate et al. ............ 324/318 |
| 7,751,866 | B2 | * | 7/2010 | Aoki et al. .................. 600/424 |
| 7,868,616 | B2 | * | 1/2011 | White et al. ................ 324/316 |
| 7,924,007 | B2 | * | 4/2011 | Arnold et al. ............... 324/309 |
| 7,944,209 | B2 | * | 5/2011 | Abe et al. ................... 324/309 |
| 7,990,140 | B2 | * | 8/2011 | Sugiura ...................... 324/307 |
| 2005/0216231 | A1 |  | 9/2005 | Aoki et al. |
| 2007/0066882 | A1 | * | 3/2007 | Maschke .................... 600/407 |
| 2010/0015918 | A1 | * | 1/2010 | Liu et al. .................... 455/41.1 |

FOREIGN PATENT DOCUMENTS

JP    2005-245963    9/2005

OTHER PUBLICATIONS

International Search Repot dated Dec. 15, 2009.

* cited by examiner

*Primary Examiner* — Brij Shrivastav
(74) *Attorney, Agent, or Firm* — Scully, Scott, Murphy & Presser, P.C.

(57) ABSTRACT

A system includes a body-insertable apparatus disposed while introduced in a subject in a detection space, and an external apparatus disposed on the outside of the subject. The body-insertable apparatus includes a first switch for connecting/interrupting a resonance circuit and an oscillation circuit or a ground line. The external apparatus includes a drive coil driving unit for outputting a drive signal having the resonance frequency; a drive coil for generating the drive magnetic field in the detection space in accordance with the drive signal; and a second switch for connecting/interrupting the drive coil driving unit and the drive coil. The second switch connects the drive coil driving unit and the drive coil when the first switch is off, and disconnects them when the first switch is on. The resonance circuit generates the resonance magnetic field in accordance with the induction signal or the drive magnetic field.

19 Claims, 17 Drawing Sheets

POSITION DETECTING SYSTEM AND POSITION DETECTING METHOD

CROSS-REFERENCE TO RELATED APPLICATIONS

This application is a continuation of PCT international application Ser. No. PCT/JP2009/069446 filed on Nov. 16, 2009 which designates the United States, incorporated herein by reference.

BACKGROUND OF THE INVENTION

1. Field of the Invention

The invention relates to a position detecting system and a detecting method and, more particularly, to a position detecting system and a position detecting method for detecting the position of a capsule body-insertable apparatus which is introduced in a subject by using a magnetic field.

2. Description of the Related Art

In recent years, a capsule body-insertable apparatus having an imaging device (hereinbelow, called a capsule endoscope) is developed. The capsule endoscope is introduced into a subject, for example, via the oral route, captures an image of the inside of the subject, and transmits the obtained image (hereinbelow, called an in-vivo image) to an apparatus disposed on the outside of the subject by radio. The operator can diagnose a symptom or the like of the subject by visually recognizing the in-vivo image received by the outside apparatus.

Such a capsule endoscope usually cannot move in a subject by itself and is moved in a subject by peristaltic movement of digestive organs of the subject. Consequently, there is a case such that, for example, as compared with an endoscope with which an observation region can be selected by the operator freely to a certain degree such as a fiber scope, the observation capability of the capsule endoscope is lower.

An example of techniques for solving such a drawback is the technique disclosed in Japanese Laid-open Patent Publication No. 2005-245963. According to the conventional art, by applying a magnetic field (hereinbelow, called a guidance magnetic field) from the outside of a subject to a capsule endoscope having magnetic field generating means such as a permanent magnet, the posture and movement of the capsule endoscope can be positively controlled from the outside of the subject.

In order to control the posture and movement of the capsule endoscope in the subject by the magnetic field applied from the outside of the subject like in the conventional art, however, the position, direction, and the like of the capsule endoscope in the subject have to be known accurately. In the following, detection of the position and direction (posture) of the capsule endoscope will be simply called position detection.

In the conventional art, by providing a resonance circuit having a coil (L) and a capacitor (C) (hereinbelow, called an LC resonance circuit) in the capsule endoscope and detecting an induced magnetic field generated by a magnetic field applied from the outside (hereinbelow, called a drive magnetic field) by the LC resonance circuit, the position and direction of the capsule endoscope are detected. In the following, the method of deriving information of the position, direction, and the like from the induced magnetic field generated by applying the drive magnetic field to the LC resonance circuit from the outside will be called a passive method.

The conventional art also describes a configuration that a resonance frequency signal is supplied to the LC resonance circuit mounted on the capsule endoscope and an excitation magnetic field generated by the signal is detected, thereby detecting the position and direction of the capsule endoscope. In the following, a method of deriving information such as position and direction from an excitation magnetic field generated by applying a resonance frequency signal to the LC resonance circuit will be called an active method.

SUMMARY OF THE INVENTION

A position detecting system according to an aspect of the present invention includes a body-insertable apparatus disposed in a state where it is introduced in a subject in a detection space; and an external apparatus disposed on the outside of the subject. The body-insertable apparatus includes an oscillation circuit that outputs an induction signal of a resonance frequency; a resonance circuit that generates a resonance magnetic field having the resonance frequency in accordance with the induction signal output from the oscillation circuit or a drive magnetic field having the resonance frequency generated in the detection space, and is connected between the oscillation circuit and a ground line; and a first switch that connects and interrupts the resonance circuit and the oscillation circuit or the ground line. The external apparatus includes a drive coil driving unit that outputs a drive signal having the resonance frequency; a drive coil that generates the drive magnetic field in the detection space in accordance with the drive signal; a second switch that connects and interrupts the drive coil driving unit and the drive coil; a magnetic field sensor that detects the resonance magnetic field; and a position deriving unit that derives position information of the body-insertable apparatus by using information of the resonance magnetic field detected by the magnetic field sensor. The second switch connects the drive coil driving unit and the drive coil when the first switch is in an off state, and disconnects the drive coil driving unit and the drive coil when the first switch is in an on state. The resonance circuit generates the resonance magnetic field in accordance with the induction signal or the drive magnetic field.

A position detecting system according to another aspect of the present invention includes a body-insertable apparatus disposed in a state where it is introduced in a subject in a detection space; and an external apparatus disposed on the outside of the subject. The body-insertable apparatus includes an oscillating means for outputting an induction signal of a resonance frequency; a resonance means for generating a resonance magnetic field having the resonance frequency in accordance with the induction signal output from the oscillating means or a drive magnetic field having the resonance frequency generated in the detection space, the resonance means being connected between the oscillating means and a ground line; and a first switching means for connecting and interrupting the resonance means and the oscillating means or the ground line. The external apparatus includes a drive signal outputting means for outputting a drive signal having the resonance frequency; a drive magnetic field generating means for generating the drive magnetic field in the detection space in accordance with the drive signal; a second switching means for connecting and interrupting the drive signal outputting means and the drive magnetic field generating means; a magnetic field detecting means for detecting the resonance magnetic field; and a position deriving means for deriving position information of the body-insertable apparatus by using information of the resonance magnetic field detected by the magnetic field detecting means. The second switching means connects the driving signal output means and the drive magnetic field generating means when the first switching means is in an off state, and disconnects the drive signal outputting means and the drive magnetic field generating means when the first switching means is in an on state. The resonance means generates the resonance magnetic field in accordance with the induction signal or the drive magnetic field.

A position detecting method according to still another aspect of the present invention is for detecting position in a subject of a body-insertable apparatus including a resonance circuit that generates a resonance magnetic field spontaneously or being induced by an external magnetic field. The position detecting method includes a resonance magnetic field intensity detecting step of detecting intensity of the resonance magnetic field; a resonance magnetic field intensity determining step of determining whether the magnetic field intensity detected at the resonance magnetic field intensity detecting step is equal to or larger than a predetermined value; an external magnetic field generating step, when the magnetic field intensity is smaller than the predetermined value, of generating the external magnetic field; a resonance magnetic field detecting step of detecting a resonance magnetic field spontaneously generated by the resonance circuit or a resonance magnetic field generated by being induced by the external magnetic field generated at the external magnetic field generating step; and a position deriving step of deriving position information indicative of a position in the subject of the body-insertable apparatus based on the resonance magnetic field detected at the resonance magnetic field detecting step.

The above and other features, advantages and technical and industrial significance of this invention will be better understood by reading the following detailed description of presently preferred embodiments of the invention, when considered in connection with the accompanying drawings.

DETAILED DESCRIPTION OF THE PREFERRED EMBODIMENTS

Figure 1:
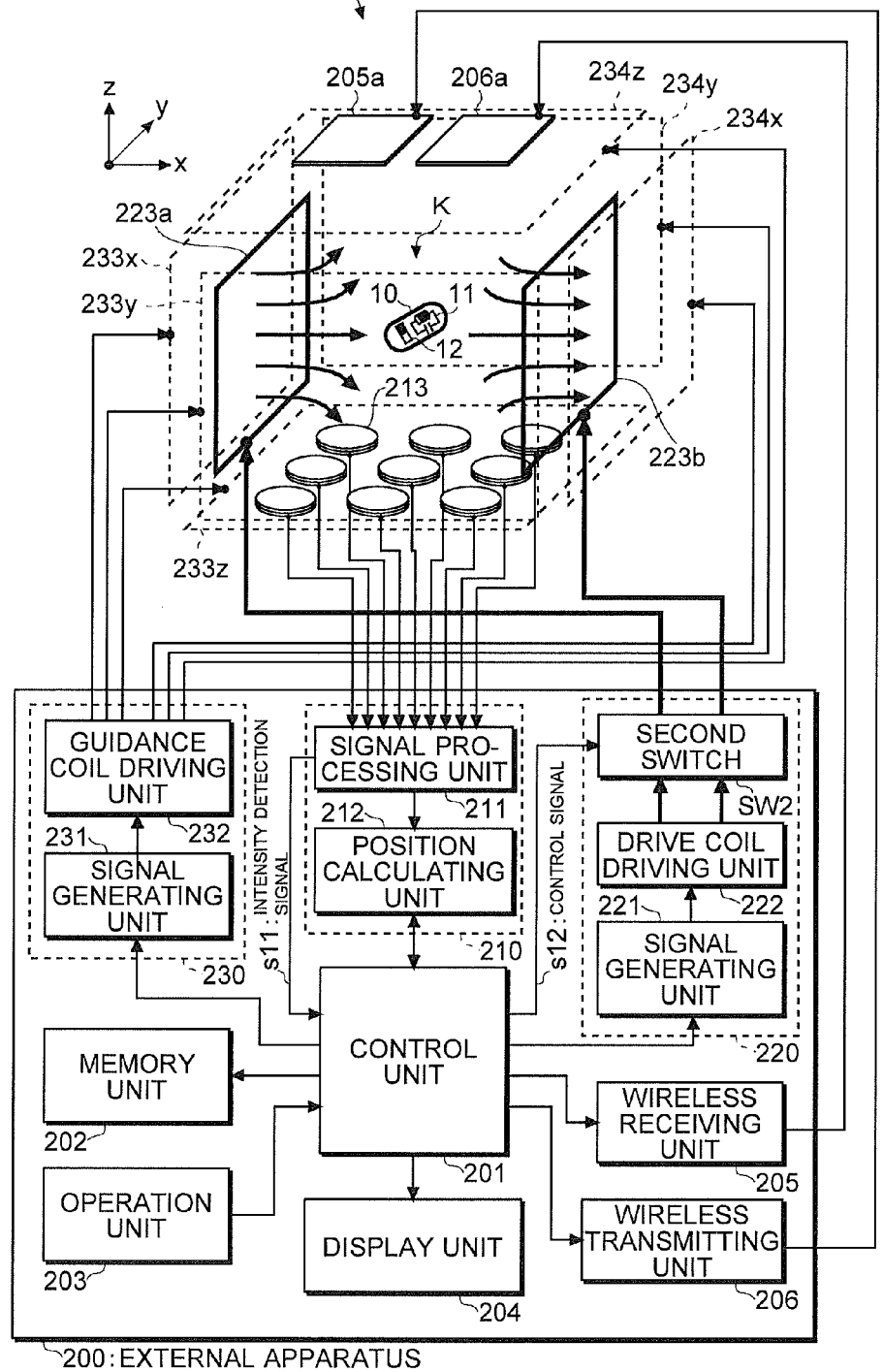
FIG. 1 is a schematic diagram showing a schematic configuration of a position detecting magnetic guidance system according to any of first to third embodiments of the invention.

Some modes for carrying out the invention will be described in detail below with reference to the drawings. In the following description, the drawings just schematically show shapes, sizes, and positional relations to a degree that the content of the invention can be understood. Therefore, the invention is not limited to the shapes, sizes, and positional relations shown in the drawings. In the drawings, to clearly show the configuration, a part of hatching in cross sections is omitted. Further, numerical values exemplified in the following description are just preferable examples of the invention. Therefore, the invention is not limited to the numerical values exemplified.

First Embodiment

In the following, the configuration and operation of a position detecting magnetic guidance system 1 according to a first embodiment of the invention will be described in detail with reference to the drawings. In the embodiment, the case will be described as an example such that, in the initial stage, position detection in the active method (hereinbelow, called active mode) is performed. When power source voltage VCC supplied from a capsule internal power source 17 in a capsule medical device 10 becomes smaller than reference voltage Vref, position detection in the passive method (hereinbelow, called passive mode) is performed for the purpose of reducing power consumption in the capsule medical device 10.

Configuration

FIG. 1 is a schematic diagram showing a schematic configuration of the position detecting magnetic guidance system 1 according to the first embodiment. As shown in FIG. 1, the position detecting magnetic guidance system 1 has a detection space K enclosing a subject in which the capsule medical device 10 is introduced, and includes \an external apparatus 200 that detects the position and the orientation (posture) of the capsule medical device 10 in the detection space K and that guides the capsule medical device 10 in a direction and orientation desired by the operator.

Capsule Medical Apparatus

Figure 2:
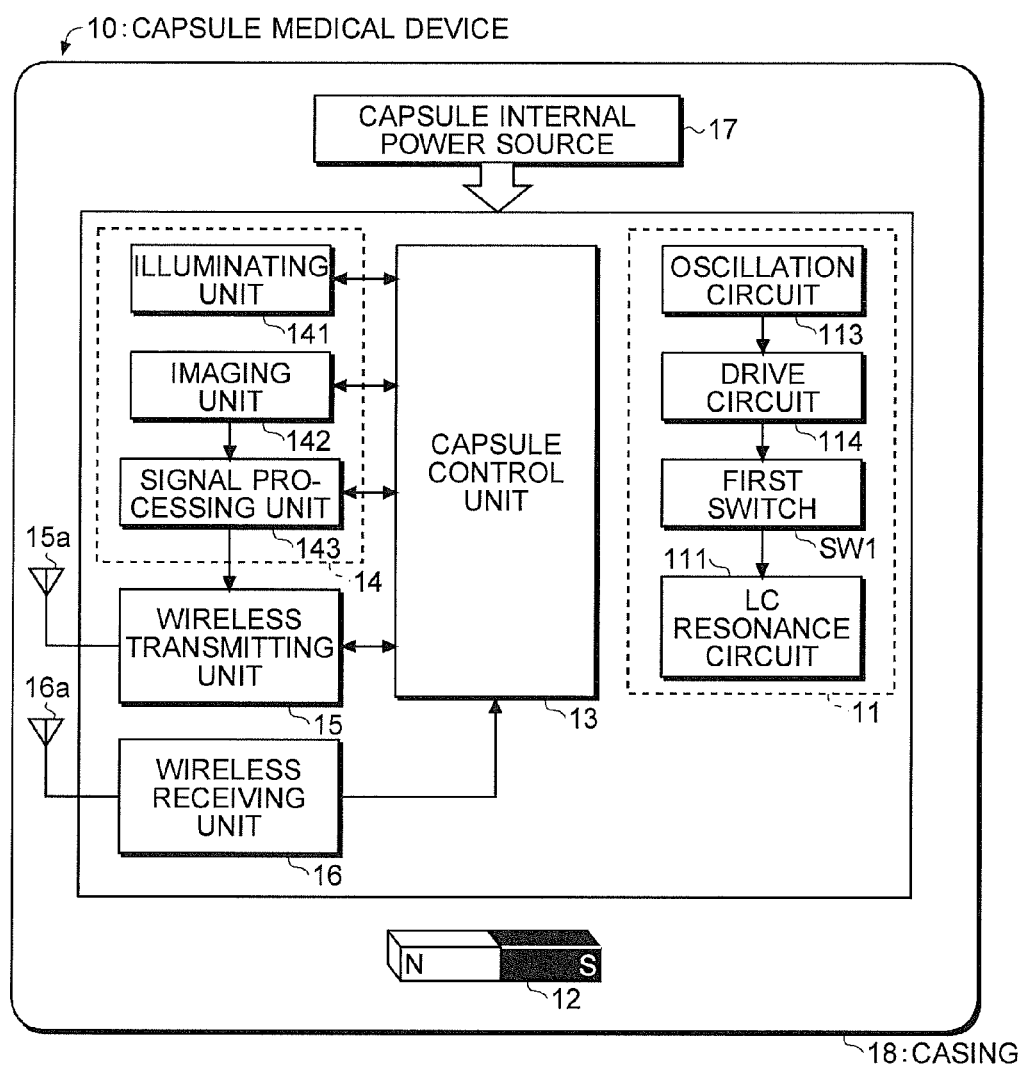
FIG. 2 is a block diagram showing a schematic configuration of a capsule medical device according to the first or second embodiment of the invention.

The capsule medical device 10 includes not only a resonance magnetic field generator 11 for generating resonance magnetic field for position detection (resonance magnetic field to be described later) and a magnetic field generator 12 (refer to FIG. 1) for guiding the capsule medical device 10 by using an external magnetic field (guidance magnetic field which will be described later) but also, as shown in FIG. 2, for example, a capsule control unit 13 for controlling the parts in the capsule medical device 10, an in-vivo information acquiring unit 14 for acquiring various information in the subject; a wireless transmitting unit 15 and a transmitting antenna 15a for transmitting in-vivo information acquired by the in-vivo information acquiring unit 14 as wireless signals to the outside of the capsule medical device 10; a wireless receiving unit 16 and a receiving antenna 16a for receiving various operation instructions and the like transmitted as wireless signals from the external apparatus 200; and a capsule internal power source 17 for supplying power to the components in the capsule medical device 10.

The in-vivo information acquiring unit 14 has: an imaging unit 142 for acquiring an in-vivo image as in-vivo information; an illuminating unit 141 for illuminating the inside of the subject at the time of imaging the inside of the subject by the imaging unit 142; and a signal processing unit 143 for executing a predetermined signal process on the in-vivo image acquired by the imaging unit 142.

Figure 3:
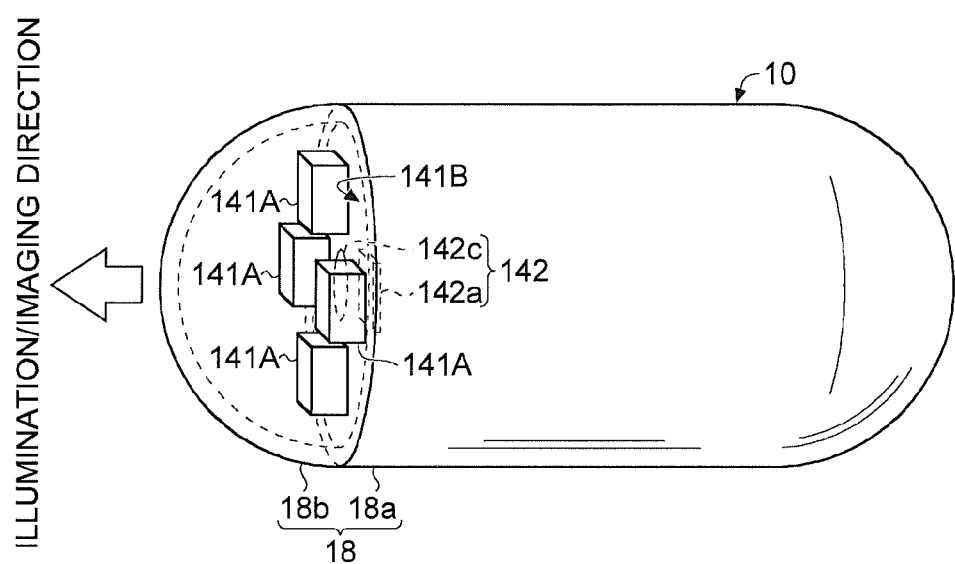
FIG. 3 is an appearance view showing a schematic configuration of the capsule medical device according to any of the first to third embodiments of the invention.

The imaging unit 142 includes, for example, as shown in FIG. 3, an imaging device 142a for converting incident light to an electric signal and forming an image, an objective lens 142c disposed on a light reception plane side of the imaging device 142a, and a not-shown imaging device drive circuit for driving the imaging device 142a. As the imaging device 142a, for example, a Charge Coupled Device (CCD) camera, a Complementary Metal Oxide Semiconductor (CMOS) camera, or the like can be used. The imaging device drive circuit drives the imaging device 142a under control of the capsule control unit 13 to acquire an in-vivo image as an analog signal. The imaging device drive circuit outputs the in-vivo image as an analog signal read from the imaging device 142a to the signal processing unit 143.

As each of light sources 141A, for example, a Light Emitting Diode (LED) or the like can be used. The light source drive circuit drives the light sources 141A in accordance with driving of the imaging unit 142 under control of the capsule control unit 13 to illuminate the inside of the subject.

The signal processing unit 143 executes predetermined signal processes such as sampling, amplification, and Analog to Digital (A/D) conversion on an analog in-vivo image input from the imaging unit 142 to thereby generate a digital in-vivo image. The in-vivo image subjected to the various processes is input to the wireless transmitting unit 15.

The in-vivo information acquiring unit 14 may include a not-shown sensor device and a sensor device drive circuit for driving the sensor device. The sensor device includes, for example, a thermometer, a pressure meter, a pH meter, and the like and properly obtains temperature, pressure, pH value, and the like in the subject as subject in-vivo information. The sensor device drive circuit drives the sensor device to obtain the in-vivo information and supplies it to the wireless transmitting unit 15 under control of the capsule control unit 13.

The wireless transmitting unit 15 is connected to the transmitting antenna 15a constructed by a coil antenna or the like, executes various processes such as superposition, modulation, up-conversion, and the like to a transmission reference frequency signal on the in-vivo information such as an in-vivo image input from the signal processing unit 143 and, after that, transmits the resultant signal as a wireless signal from the transmitting antenna 15a to the external apparatus 200. That is, the wireless transmitting unit 15 also functions as an in-vivo information transmitting unit (for example, an image transmitting unit) for transmitting in-vivo information (for example, an in-vivo image) acquired by the in-vivo information acquiring unit 14 (for example, an imaging unit) to the external apparatus 200.

The wireless receiving unit 16 is connected to the receiving antenna 16a constructed by a coil antenna or the like, receives various operation instructions and the like transmitted as wireless signals from the external apparatus 200 via the receiving antenna 16a, executes various processes such as filtering, down-conversion, demodulation, decoding, and the like on the received signals, and outputs the resultant signals to the capsule control unit 13.

The capsule control unit 13 is constructed by, for example, a Central Processing Unit (CPU), a Microprocessor Unit (MPU), or the like, and controls the components in the capsule medical device 10 by reading and executing a program and parameters read from a not-shown memory unit on the basis of the various operation instructions and the like input from the external apparatus 200 via the wireless receiving unit 16.

The capsule internal power source 17 includes, for example, a button cell such as a primary cell or secondary cell, a power supply circuit for boosting power output from the button cell and supplying the boosted power to the components in the capsule medical device 10, and the like, and supplies drive power to the components in the capsule medical device 10.

As the magnetic field generator 12, for example, a permanent magnet or the like can be used. However, it is not limited to a permanent magnet but any configuration which is magnetized by a magnetic field input from the outside and makes the capsule medical device 10 generate driving power, rotational force, or the like.

The resonance magnetic field generator 11 includes: an LC resonance circuit 111 emitting a magnetic field (excited magnetic field) by being excited by a magnetic field for position detection (hereinbelow, called drive magnetic field) input from the outside or emitting a magnetic field (hereinbelow, called induced magnetic field) by being induced by a frequency signal (hereinbelow, called an induction signal) having a resonance frequency F0 input from the outside; an oscillation circuit 113 that oscillates at the resonance frequency F0; a first switch SW1 for switching conduction/interruption between the oscillation circuit 113 and the LC resonance circuit 111; and a drive circuit 114 (first switch controller) for turning on/off the first switch SW1 in accordance with the voltage level of the power source voltage VCC output from the capsule internal power source 17 (refer to FIG. 2). The resonance frequency F0 is a resonance frequency of the LC resonance circuit 111. In the following description, the excited magnetic field and the induced magnetic field may be also simply collectively called resonance magnetic field.

The capsule medical device 10 has, as its operation modes, an active mode and a passive mode. When the capsule medical device 10 operates in the active mode, the first switch SW1 is turned on and a guide signal having the resonance frequency F0 is supplied from the oscillation circuit 113 to the LC resonance circuit 111. In such a manner, an induced magnetic field is emitted from the LC resonance circuit 111. When the capsule medical device 10 operates in the passive mode, the first switch SW1 is turned off, and the LC resonance circuit 111 and the oscillation circuit 113 are electrically separated from each other. Therefore, the LC resonance circuit 111 emits the excitation magnetic field by being excited by the drive frequency having a frequency almost the same as the resonance frequency F0, which is supplied from the outside. An example of the configuration of the resonance magnetic field generator 11 will be described in detail later with reference to the drawings.

The above-described components (11, 12, 13, 14, 15, 15a, 16, 16a, 17, and SW1) are housed in a capsule-shaped casing 18. As shown in FIG. 3, the casing 18 is made by a container 18a having an almost cylindrical shape or a semi-ellipse spherical shape whose one end has a hemispherical dome shape and whose other end is open, and a cap 18b having a hemispherical shape and, when being fit in the opening in the container 18a, water-tightly sealing the casing 18. The casing 18 has, for example, a size to a degree that it can be swallowed by the subject. In the embodiment, at least the cap 18b is formed of a transparent material. The light sources 141A are mounted on a circuit board 141B on which the above-described light source drive circuit (not shown) is mounted. Similarly, the imaging device 142a and the objective lens 142c are mounted on a circuit board (not shown) on which an imaging device drive circuit (not shown) is mounted. The circuit board 141B on which the light sources 141A are mounted and the circuit board on which the imaging device 142a is mounted are disposed on the cap 18b side in the casing 18. The device mounting face of each of the circuit boards is oriented toward the cap 18b side. Therefore, as shown in FIG. 3, the imaging/illuminating direction of the imaging device 142a and the light sources 141A is oriented to the outside of the capsule medical device 10 via the transparent cap 18b.

Detection Space

Referring again to FIG. 1, the description will be continued. In the detection space K, drive coils 223a and 223b for generating an almost uniform drive magnetic field in the detection space K, a plurality of sense coils 213 for detecting the resonance magnetic field generated by the LC resonance circuit 111 of the capsule medical device 10, and guidance coils 233x and 234x, 233y and 234y, and 233z and 234z for guiding the position and direction (posture) of the capsule medical device 10 are disposed.

The drive coils 223a and 223b are disposed, for example, so as to be opposed to each other while sandwiching the detection space K. In the embodiment, for example, the two opposed drive coils 223a and 223b are disposed so as to generate an almost uniform drive magnetic field in the x-axis direction (refer to FIG. 1) in the detection space K.

Each of the sense coils 213 is, for example, a magnetic sensor made of three coils capable of detecting the magnetic field intensity and direction in three axes (in FIG. 1, x axis, y axis, and z axis). The plurality of sense coils 213 are, for example, disposed in positions where they are not so influenced by the drive magnetic field and the resonance magnetic field generated by the LC resonance circuit 111 is easily detected. In the embodiment, the plurality of sense coils 213 are disposed on the bottom face of the detection space K (the x-y plane on the lower side of the detection space K). The invention, however, is not limited to the configuration. Each of the sense coils 213 is not limited to a magnetic sensor made by a coil but can be constructed by, for example, a magnetic sensor made by a magnetoresistive element, a magnetic impedance element (MI element), or the like. Each of the sense coils 213 can be also made by a uniaxial magnetic sensor or the like.

The guidance coils 233x and 234x, 233y and 234y, and 233z and 234z are disposed so as to surround the detection space K. For example, the guidance coils 233x and 234x are disposed so as to sandwich the detection space K in the x-axis direction and simultaneously driven, thereby generating a guidance magnetic field that controls the position and direction of the capsule medical device 10. Similarly, the guidance coils 233y and 234y are disposed and the guidance coils 233z and 234z are disposed so as to sandwich the detection space K in the y-axis direction or z-axis direction and simultaneously driven, thereby generating a guidance magnetic field that controls the position and direction of the capsule medical device 10. The combination to be driven is properly selected on the basis of the direction and orientation of moving the capsule medical device 10.

External Apparatus

The external apparatus 200 includes: a drive magnetic field generator 220 for supplying a signal (hereinbelow, called a drive signal) for generating drive magnetic fields used in a passive mode to the drive coils 223a and 223b; a position deriving unit 210 for deriving the position and direction of the capsule medical device 10 from a voltage change (hereinbelow, called a detection signal) obtained by the sense coil 213; a capsule guidance unit 230 for supplying a signal (guidance signal) for making the guidance coils 233x to 233z and 234x to 234z properly generate a guidance magnetic field for controlling the position and direction of the capsule medical device 10; a control unit 201 for controlling the components in the external apparatus 200; a memory unit 202 for storing various programs and parameters executed when the control unit 201 controls the components; an operation unit 203 for inputting various operation instructions to the capsule medical device 10 by the operator; a display unit 204 for displaying information of the position and direction (hereinbelow, simply called position information or the like) of the capsule medical device 10 and in-vivo information obtained from the capsule medical device 10 in the form of an image (including a video image) and sound; a wireless receiving unit 205 and a receiving antenna 205a for receiving in-vivo information and the like transmitted as a wireless signal from the capsule medical device 10; and a wireless transmitting unit 206 and a transmitting antenna 206a for transmitting various operation instructions such as an imaging instruction as wireless signals to the capsule medical device 10.

The control unit 201 is constructed by, for example, a CPU, an MPU, or the like, and controls the components in the external apparatus 200 in accordance with a program and parameters read from the memory unit 202.

The memory unit 202 is constructed by, for example, a Random Access Memory (RAM), a Read Only Memory (ROM), and the like and holds programs and parameters which are executed when the control unit 201 controls the components. The memory unit 202 properly holds the in-vivo image received from the capsule medical device 10 and position information such as the position, direction, and the like of the capsule medical device 10 derived by the position deriving unit 210.

The operation unit 203 is constructed by, for example, a keyboard, a mouse, a numerical keypad, a joystick, and the like and used by the operator to enter various operation instructions to the capsule medical device 10 such as an imaging instruction (including other in-vivo information acquiring instructions) and various operation instructions to the external apparatus 200 such as a movement instruction at the time of guiding the capsule medical device 10 and a screen switching instruction of switching a screen to be displayed on the display unit 204. The function of switching a screen to be displayed on the display unit 204 may be provided in the case where the capsule medical device 10 includes a plurality of imaging units 142 and images acquired by the capsule medical device 10 are displayed in an almost real-time manner on the display unit 204.

The display unit 204 is a display device such as a liquid crystal display, a plasma display, or an LED array and displays the position information and the like of the capsule medical device 10 and in-vivo information such as an in-vivo image transmitted from the capsule medical device 10. On the display unit 204, a voice reproducing function using a speaker or the like may be mounted. Using the sound reproducing function, the display unit 204 notifies the operator of various operation guidances and information (including a warning) such as a battery remaining amount of the capsule medical device 10 by sound.

The wireless receiving unit 205 is connected to the receiving antenna 205a such as a dipole antenna disposed close to the detection space K, receives an in-vivo image or the like transmitted as a wireless signal from the capsule medical device 10 via the receiving antenna 205a, executes various processes such as filtering, down-conversion, demodulation, decoding, and the like on the received signal, and outputs the resultant signal to the control unit 201. That is, the wireless receiving unit 205 also functions as an in-vivo information receiving unit (for example, an image receiving unit) that receives the in-vivo information (for example, an in-vivo image) transmitted from the capsule medical device 10.

The wireless transmitting unit 206 is connected to the transmitting antenna 206a such as a dipole antenna disposed close to the detection space K, executes various processes such as superimposing, modulation, up-conversion, and the like to a transmission reference frequency signal on signals such as various operation instructions to the capsule medical device 10, input from the control unit 201 and, after that, transmits the resultant signal as an electric wave signal from the transmitting antenna 206a to the capsule medical device 10.

The drive magnetic field generator 220 includes a signal generating unit 221, a drive coil driving unit 222, and a second switch SW2. The signal generating unit 221 calculates a signal waveform having a frequency almost equal to the resonance frequency F0 of the LC resonance circuit 111 in the capsule medical device 10 in accordance with a control signal input from the control unit 201, generates a drive signal having the signal waveform, and outputs it to the drive coil driving unit 222.

The drive coil driving unit 222 current-amplifies the drive signal input from the signal generating unit 221 and inputs the amplified drive signal to the drive coils 223a and 223b via the second switch SW2. The drive coils 223a and 223b to which the amplified drive signal is input emit a magnetic field having a frequency almost equal to the resonance frequency F0 of the LC resonance circuit 111 in the capsule medical device 10, thereby generating a drive magnetic field which makes the LC resonance circuit 111 excited in the detection space K. The current amplification factor by the drive coil driving unit 222 is set in consideration of the processing capability (such as dynamic range) of the sense coil 213 and a signal processing unit 211 which will be described later, the S/N ratio of a detection signal obtained by a sense coil 213, and the like.

The second switch SW2 switches a connection state between the drive coil driving unit 222 and the drive coils 223a and 223b in accordance with a control signal s12 received from the control unit 201. Specifically, in the case of operation in the active mode, the control unit 201 inputs, for example, the control signal s12 of the low level to the second switch SW2. By the signal, the second switch SW2 is turned off, and the connection between the drive coil driving unit 222 and the drive coils 223a and 223b is interrupted. In this state, the drive magnetic field by the drive coils 223a and 223b is not generated in the detection space K. On the other hand, in the case of operation in the passive mode, the control unit 201 inputs, for example, the control signal s12 of the high level to the second switch SW2. By the signal, the second switch SW2 is turned on, and the connection between the drive coil driving unit 222 and the drive coils 223a and 223b is established. In this state, the drive signal output from the drive coil driving unit 222 is supplied to the drive coils 223a and 223b via the second switch SW2 and a drive magnetic field is generated in the detection space K.

In the active mode, as described above, the induced magnetic field of the resonance frequency F0 is emitted from the LC resonance circuit 111 of the capsule medical device 10 introduced in the subject into the detection space K. On the other hand, in the passive mode, as described above, a drive magnetic field having the frequency almost equal to the resonance frequency F0 is generated by the drive coils 223a and 223b in the detection space K. Therefore, the excitation magnetic field having the resonance frequency F0 is emitted from the LC resonance circuit 111.

The phase of the resonance magnetic field emitted from the LC resonance circuit 111 during operation in the passive mode is behind that of the drive magnetic field generated by the drive coils 223a and 223b by about 90 degrees. Therefore, the phase of the resonance magnetic field is deviated from that of the drive signal input to the drive coils 223a and 223b by about 90°. In the embodiment, by using the phase difference, the resonance magnetic field is separated from the drive magnetic field in a position calculating unit 212 which will be described later (calibration process).

The position deriving unit 210 derives, in an almost real-time manner, the position and direction (position information or the like) of the capsule medical device 10 by executing a predetermined process (position detecting process which will be described later) according to the active and passive modes using information of a magnetic field (hereinbelow, called magnetic field information) included in a detection signal detected by the sense coil 213.

The position deriving unit 210 includes, for example, the signal processing unit 211 and the position calculating unit 212. The signal processing unit 211 receives each of the detection signals detected by the plurality of sense coils 213. The signal processing unit 211 properly performs amplification, band limitation, Analog to Digital (A/D) conversion, and Fast Fourier Transform (FFT) on the input detection signals and outputs the processed detection signals. The signal processing unit 211 periodically receives the detection signals from the sense coil 213, executes the above-described signal processes on the input signals and, after that, supplies the resultant signals to the position calculating unit 212. The detection signal is a signal expressing, in voltage, magnetic field information such as intensity and direction of the magnetic field. The band limitation is executed to eliminate a frequency component deviated from the resonance frequency F0 by a predetermined bandwidth or more, such as information of the guidance magnetic field (hereinbelow, called guidance magnetic field information), information of noise, and the like from the detection signal.

The position calculating unit 212 derives the present position information and the like of the capsule medical device 10 from the magnetic field information included in the detection signal by executing a predetermined arithmetic process on the detection signal entered from the signal processing unit 211.

The position calculating unit 212 outputs the derived position information and the like to the control unit 201.

The detection signal input to the position calculating unit 212 includes not only the information of the resonance magnetic field or self-induced magnetic field (hereinbelow, called resonance magnetic field information) emitted from the LC resonance circuit 111 but also information of an unnecessary magnetic field (hereinbelow, called unnecessary magnetic field) having a frequency almost equal to the resonance frequency F0. The unnecessary magnetic fields include a magnetic field emitted from a coil (such as the guidance coils 233x to 233z and 234x to 234z and the drive coils 223a and 223b) disposed close to the detection space K and excited by the resonance magnetic field emitted from the LC resonance circuit 111 and a drive magnetic field emitted from the drive coils 223a and 223b.

The unnecessary magnetic field as described above can be reduced by reducing the number of coils disposed in a valid state near the detection space K. In the embodiment, in the active mode, the drive coils 223a and 223b which are not used are electrically disconnected from the drive coil driving unit 222 by using the second switch SW2 to be described later. With the configuration, in the active mode, the drive coils 223a and 223b can be prevented from being disposed near the detection space K in a state where a closed circuit is formed by the output impedance of the drive coil driving unit 222, so that the unnecessary magnetic field information included in the detection signal to be input to the position calculating unit 212 can be reduced. As a result, the position detection precision in the active mode can be improved. Since a calibration process which will be described later becomes unnecessary by the configuration, a position detecting process which will be described later in the active mode can be simplified.

On the other hand, in the passive mode, the drive magnetic field is emitted from the drive coils 223a and 223b. Consequently, the detection signal output from the signal processing unit 211 includes, as unnecessary magnetic field information, not only the resonance magnetic field information desired to be obtained, information (hereinbelow, called guidance coil unnecessary magnetic field information) of a magnetic field (hereinbelow, called guidance coil unnecessary magnetic field) emitted from the guidance coils 233x to 233z and 234x to 234z excited by the resonance magnetic field, information (hereinbelow, called drive coil unnecessary magnetic field information) of the magnetic field (hereinbelow, called drive coil unnecessary magnetic field) emitted by the drive coils 223a and 223b excited by the resonance magnetic field, and information of the drive magnetic field (hereinbelow, called drive magnetic field information) emitted from the drive coils 223a and 223b driven.

Consequently, in the embodiment, a process for eliminating the drive coil unnecessary magnetic field information, a process for eliminating the guidance coil unnecessary magnetic field information, and a process for eliminating the drive magnetic field information are executed on the detection signal output from the signal processing unit 211. It enables only the resonance magnetic field information to be extracted from the detection signal, so that high-precision position detection becomes possible. In the following description, a process of deriving the position information or the like of the capsule medical device 10 from the detection signal will be called a position detecting process. A process of eliminating the drive magnetic field information from the detection signal will be called a calibration process. A process of eliminating guidance coil unnecessary magnetic field information and/or drive coil unnecessary magnetic field information from the detection signal will be called a position information deriving process.

The position information or the like output from the position calculating unit 212 is entered to the control unit 201. The control unit 201 displays the information such as the present position and direction of the capsule medical device 10 on the display unit 204 by using the input position information or the like. The operator can recognize the present position and direction of the capsule medical device 10 from the display unit 204.

The signal processing unit 211 measures signal intensity of a signal detected by the sense coil 213. In other words, the signal processing unit 211 also functions as a signal intensity detecting unit for detecting intensity of a signal detected by the sense coil 213.

A signal indicative of measured signal intensity (hereinbelow, called intensity detection signal) s11 is input to the control unit 201. The control unit 201 switches its operation between the active mode and the passive mode on the basis of signal intensity notified by the intensity detection signal s11. For example, in an initial state, the control unit 201 operates in the active mode. After that, when the power source voltage VCC output from the capsule internal power source 17 in the capsule medical device 10 drops, the self induced magnetic field by the LC resonance circuit 111 is weakened. As a result, in the case where the intensity of the signal detected by the sense coil 213 becomes smaller than a preset specified value, the control unit 201 switches its operation mode to the passive mode. As described above, the control unit 201 also functions as a second switch control unit for controlling the on/off state of the second switch SW2 on the basis of the signal intensity detected by the signal processing unit 211 also functioning as the signal intensity detecting unit.

In the active mode, the control unit 201 outputs the control signal s12 which turns off the second switch SW2, thereby electrically interrupting between the drive coil drive coil driving unit 222 and the drive coils 223a and 223b. On the other hand, in the passive mode, the control unit 201 outputs the control signal s12 which turns on the second switch SW2, thereby electrically connecting the drive coil driving unit 222 and the drive coils 223a and 223b, and making the signal generating unit 221 generate a drive signal having a frequency almost equal to the resonance frequency F0. In the following, the process of switching the operation mode between the active mode and the passive mode including the control on the second switch SW2 will be called a mode switching process.

The operator can enter an operation instruction of operating the position and direction of the capsule medical device 10 with the operation unit 203. Further, the operator can also enter an instruction of obtaining in-vivo information to the capsule medical device 10 using the operation unit 203.

The control unit 201 calculates information including a guidance magnetic field (hereinbelow, called guidance information) to be given to the magnetic field generator (permanent magnet) 12 mounted on the capsule medical device 10 from the present position and direction of the capsule medical device 10 and a target position and direction entered from the operation unit 203, and supplies it to the capsule guidance unit 230. In the following description, a process of calculating guidance information and making the capsule guidance unit 230 guide the position and direction of the capsule medical device 10 will be called a guidance process.

The capsule guidance unit 230 has a signal generating unit 231 and a guidance coil driving unit 232. The guidance information calculated by the control unit 201 is input to the signal generating unit 231 in the capsule guidance unit 230. The signal generating unit 231 calculates a signal waveform necessary to generate the guidance magnetic field in accordance with the input guidance information and generates and outputs a guidance signal having the signal waveform.

The guidance signal output from the signal generating unit 231 is input to the guidance coil driving unit 232. The guidance coil driving unit 232 current-amplifies the input guidance signal and, after that, properly supplies the amplified signal to the guidance coils 233x to 233z and 234x to 234z. A magnetic field is emitted from the guidance coils 233x to 233z and 234x to 234z properly selected, and a guidance magnetic field for guiding the capsule medical device 10 to the target position and direction is generated in the detection space K. The guidance coils 233x to 233z and 234x to 234z, the guidance coil driving unit 232, and the signal generating unit 231 are prepared in the axes (the x axis, y axis, and z axis) to generate a three-dimensional guidance magnetic field in the detection space K.

Resonance Magnetic Field Generating Unit

Figure 4:
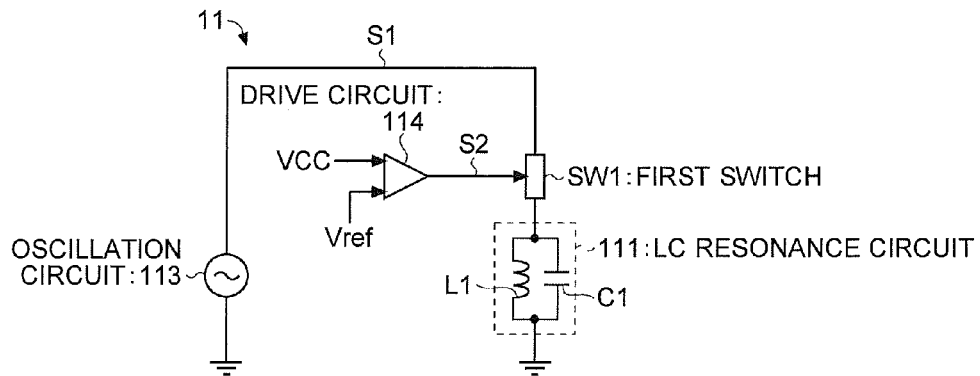
FIG. 4 is a diagram showing a schematic configuration of a resonance magnetic field generator according to the first embodiment of the invention.
Figure 5:
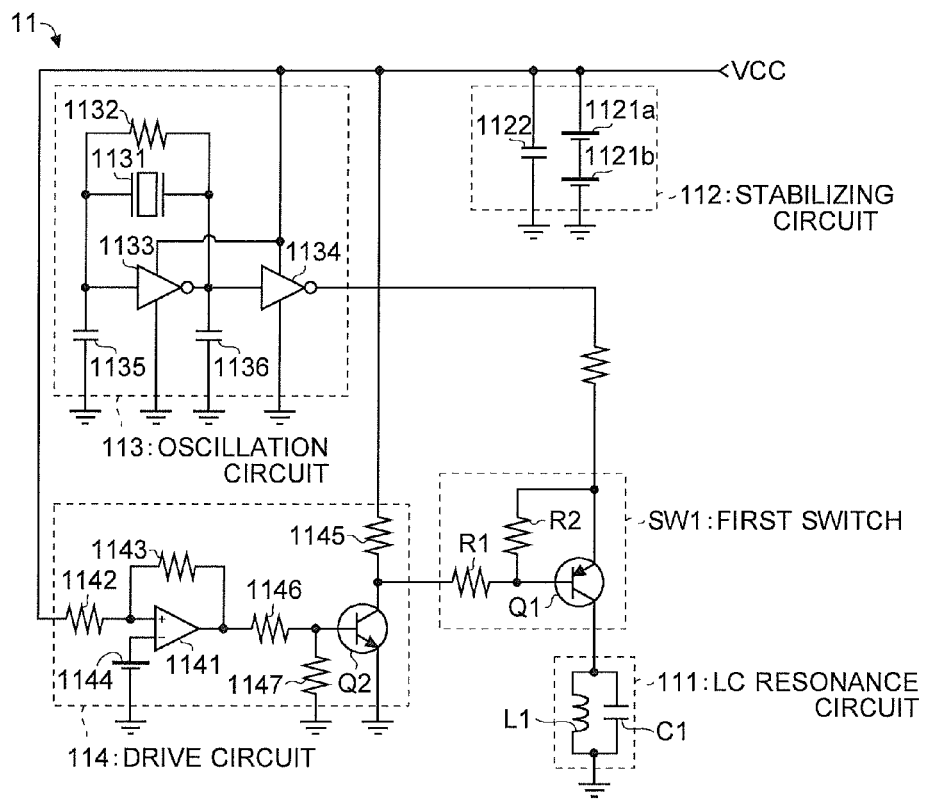
FIG. 5 is a diagram showing a circuit configuration example of the resonance magnetic field generator according to the first embodiment of the invention.

Next, the LC resonance magnetic field generator 11 in the capsule medical device 10 will be described in detail with reference to the drawings, including the LC resonance circuit 111 for emitting a resonance magnetic field, the oscillation circuit 113 for driving the LC resonance circuit 111, the drive circuit 114 for switching the operation mode of the capsule medical device 10 between the active mode and the passive mode in accordance with the level of the power supply voltage VCC output from the capsule internal power source 17, and the first switch SW1 for switching the connection state between the LC resonance circuit 111 and another circuit in accordance with the control signal s12 output from the drive circuit 114 (in other words, according to the operation mode (active mode/passive mode)). FIG. 4 is a diagram showing a schematic configuration of the resonance magnetic field generator 11 according to the embodiment. FIG. 5 is a diagram showing a circuit configuration example of the resonance magnetic field generator 11.

As shown in FIG. 4, the resonance magnetic field generator 11 has a configuration that a guidance signal S1 having the resonance frequency F0 generated when the oscillation circuit 113 oscillates is input to the LC resonance circuit 111 via the first switch SW1. The connection between the oscillation circuit 113 and the LC resonance circuit 111 is established/interrupted by turn-on/off of the first switch SW1 by the control signal S2 output from the drive circuit 114. The drive circuit 114 outputs the control signal S2 for turning on/off the first switch SW1 in accordance with the voltage level of the power source voltage VCC output from the capsule internal power source 17 (refer to FIG. 2).

As shown in FIG. 5, the LC resonance circuit 111 includes a capacitor C1 and an inductor L1 which are connected in parallel and is connected between the first switch SW1 and the ground line. In the passive mode, the drive magnetic field generated in the detection space K by the drive coils 223a and 223b is input to the LC resonance circuit 111. As described above, the drive magnetic field has a frequency almost equal to the resonance frequency F0 of the LC resonance circuit 111. Therefore, the LC resonance circuit 111 is excited by the input drive magnetic field and emits the excited magnetic field. In the active mode, the guidance signal S1 output from the oscillation circuit 113 which will be described later is input to the LC resonance circuit 111. The guidance signal S1 is a signal having a frequency almost equal to the resonance frequency F0 of the LC resonance circuit 111. Therefore, the LC resonance circuit 111 resonates by the guidance signal S1 and emits a guide magnetic field having the resonance frequency F0.

The oscillation circuit 113 is a so-called inverter oscillator including: a crystal oscillator 1131 which oscillates at a frequency according to the applied voltage; a resistor 1132 connected in parallel to the crystal oscillator 1131; two inverting amplifier circuits 1133 and 1134 for amplifying a signal (drive signal before amplification) output from the crystal oscillator 1131 in accordance with the power source voltage VCC; and two capacitors 1135 and 1136. To the crystal oscillator 1131, a voltage which oscillates the crystal oscillator 1131 at a frequency almost equal to the integral multiple of the resonance frequency F0 is applied. In the case of oscillating the crystal oscillator 1131 at a frequency of the integral multiple of the resonance frequency F0, a frequency dividing circuit for frequency-dividing a frequency signal output from the crystal oscillator 1131 is provided. The invention is not limited to the above-described VCO but various oscillation circuits such as a solid vibrator oscillation circuit using a ceramic oscillator or the like and a CR oscillation circuit constructed by a capacitor (C) and a resistor (R) can be used.

The first switch SW1 includes, for example, one transistor Q1, a resistor R1 connected to the base terminal of the transistor Q1, and a resistor R2 connected between the base and collector of the transistor Q1, and functions as a mode changing switch for switching the state of connection between the LC resonance circuit 111 and another circuit in accordance with the passive mode and the active mode. To the base of the transistor Q1, the control signal S2 output from the drive circuit 114 which will be described later is input via the resistor R1. Therefore, the first switch SW1 establishes or interrupts connection between the oscillation circuit 113 and the LC resonance circuit 111 in accordance with the control signal S2 output from the drive circuit 114. The resistors R1 and R2 are resistors for determining the base bias of the transistor Q1 and are properly changed according to the magnitude of an output of the oscillation circuit 113.

The drive circuit 114 is a so-called hysteresis comparator including a resistor 1142, a power source 1144 for outputting a reference voltage Vref, a comparison circuit 1141 having a non-inversion input terminal (+) to which the guidance signal S1 is input via the resistor 1142 and an inversion input terminal (−) to which the reference voltage Vref from the power source 1144 is input, and a resistor 1143 connected between the output terminal of the comparison circuit 1141 and the non-inversion input terminal (+). The output of the hysteresis comparator is provided with an inversion circuit for inverting an output from the comparison circuit 1141. The inversion circuit includes, for example, a transistor Q2, a resistor 1145 provided between the transistor Q2 and the power source voltage VCC, a resistor 1146 connected between the output terminal of the comparison circuit 1141 and the base of the transistor Q2, and a resistor 1147 connected between the base of the transistor Q2 and the ground line.

The drive circuit 114 functions as a switch control unit for turning on/off the first switch SW1 in accordance with the passive mode or the active mode. For example, the power source voltage VCC input to the non-inversion circuit (+) via the resistor 1142 and the reference voltage Vref input to the inversion input terminal (−) are compared with each other and the power source voltage VCC becomes below the reference voltage Vref, the drive circuit 114 outputs the control signal S2 for turning off the first switch SW1. A signal output from the comparison circuit 1141 is inverted by the inversion circuit and, after that, the inverted signal is input to the first switch SW1. The resistors 1142 and 1143 are resistors determining the input voltage of the non-inversion input terminal (+) of the comparison circuit 1141 and are properly changed according to the level of the power source voltage VCC.

The resonance magnetic field generator 11 according to the embodiment may have a stabilizing circuit 112 for stabilizing the voltage (power source voltage VCC) input to the control terminal of each of the two inverting amplifier circuits 1133 and 1134 in the oscillation circuit 113 and the non-inversion input terminal (+) of the comparison circuit 1141 in the drive circuit 114. The stabilizing circuit 112 includes, for example, a capacitor 1122 connected in series between the power source line to which the power source voltage VCC is applied and the ground line and secondary cells 1121a and 1121b similarly connected between the power source line and the ground line. The capacitor 1122 functions as a smoothing circuit for removing noise or the like entering the power source line and a high-frequency current supplying circuit operating as a high-frequency current supply source. The secondary cells 1121a and 1121b function as a circuit for preventing the voltage level of the power source voltage VCC from sharply changing at the time of driving the in-vivo information acquiring unit 14.

Operation

Now, the operation of the position detecting magnetic guidance system 1 according to the embodiment will be described in detail with reference to the drawings. The operation of the position detecting magnetic guidance system 1 according to the embodiment includes, as described above, a mode switching process of switching the operation mode between the active mode and the passive mode in accordance with signal intensity detected by the signal processing unit 211, a position detecting process of deriving position information or the like including information of the present position and direction of the capsule medical device 10 in accordance with the operation mode switched in the mode switching process, and a guidance process of making the capsule guidance unit 230 guide the position and direction of the capsule medical device 10 in accordance with the present position and direction of the capsule medical device 10 and the position and direction as guidance targets entered by the operation unit 203. The position detecting process includes a calibration process of eliminating the influence exerted on the sense coil 213 by the drive magnetic field and a position information deriving process of eliminating the influence (offset) exerted on the sense coil 213 by various coils (the drive coils 223a and 223b and the guidance coils 233x to 233z and 234x to 234z) disposed in the detection space K.

Each of the capsule medical device 10 and the external apparatus 200 has the active mode and the passive mode. The mode switching in the capsule medical device 10 is realized by using the drive circuit 114 for comparing the power source voltage VCC and the reference voltage Vref by using the circuits as described above, so that the mode switching in the capsule medical device 10 will not be described here. When the capsule medical device 10 shifts from the active mode to the passive mode, emission of the induced magnetic field from the capsule medical device 10 stops. Consequently, at the time of the shift, the signal intensity detected by the signal processing unit 211 temporarily drops. In the embodiment, the temporal drop in the signal intensity due to the stop of emission of the induced magnetic field is detected, and the external apparatus 200 is switched from the active mode to the passive mode. The invention, however, is not limited to the configuration. For example, when there is a sufficient difference between the induced magnetic field and the excitation magnetic field, a configuration may be employed such that a threshold is simply provided for the signal intensity and the operation mode of the external apparatus 200 is switched to the active mode or the passive mode in accordance with whether the signal intensity exceeds the threshold.

Mode Switching Process

Figure 6:
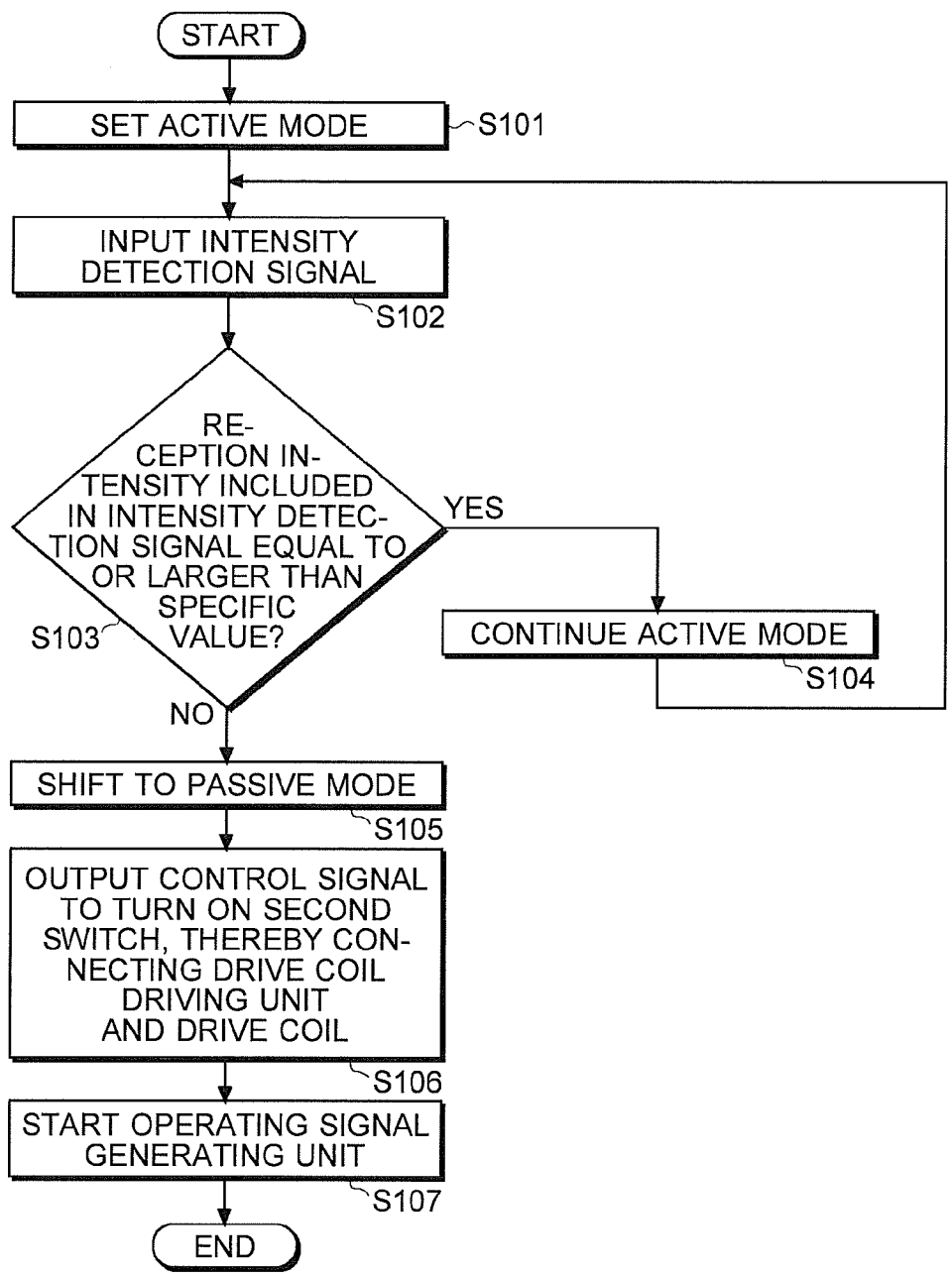
FIG. 6 is a flowchart showing outline of a mode switching process according to any of the first to third embodiments of the invention.

First, the mode switching process executed in the external apparatus 200 will be described in detail with reference to the drawings. FIG. 6 is a flowchart showing outline of the mode switching process executed in the external apparatus 200. The mode switching process is executed by the control unit 201. The embodiment relates to an example of the case where, as described above, the position detection in the active mode is performed at the initial stage and, when the power source voltage VCC supplied from the capsule internal power source 17 in the capsule medical device 10 becomes smaller than the reference voltage Vref, the position detection in the passive mode is performed. Since it is unnecessary to input the guidance signal S1 from the oscillation circuit 113 to the LC resonance circuit 111 in the passive mode, power consumption can be suppressed.

As shown in FIG. 6, when the mode switching process is started, first, the control unit 201 sets the active mode (step S101). The mode management can be realized by, for example, storing a flag for managing the mode in a predetermined storage region in the memory unit 202. In the active mode, the control unit 201 generates the control signal s12 of, for example, the low level and supplies it to the second switch SW2 to turn off the second switch SW2, thereby electrically disconnecting the drive coil driving unit 222 and the drive coils 223a and 223b. Therefore, at this stage, the drive magnetic field is not generated yet in the detection space K, and the drive coils 223a and 223b do not form a closed circuit. That is, a detection signal detected by the sense coil 213 does not include the drive magnetic field information and the drive coil unnecessary magnetic field information.

Next, the control unit 201 receives the intensity detection signal s11 (refer to FIG. 1) including the signal intensity of the detection signal from the signal processing unit 211 (refer to FIG. 1) of the position deriving unit 210 (step S102). The signal processing unit 211 periodically or always obtains the signal intensity of the detection signal detected by the sense coil 213, generates the intensity detection signal s11 expressing the signal intensity in voltage level, and supplies it to the control unit 201.

When the intensity detection signal s11 is received from the signal processing unit 211, the control unit 201 determines whether the reception intensity included in the intensity detection signal s11 is equal to or larger than a predetermined specific value (step S103). The determination can be made by, for example, specifying a specific value by the reference voltage and comparing the voltage level of the intensity detection signal s11 expressing the signal intensity in voltage level with the reference voltage by a digital process or analog process. The determination in step S103 may be made by detecting whether the intensity detection signal s11 is below the specific value for a predetermined period. It can prevent erroneous operation caused by unexpected detection of no detection signal or the like.

In the case where the reception intensity is equal to or larger than the specific value as a result of the determination in step S103 (Yes in step S103), the control unit 201 continues the active mode (step S104) and returns to step S102.

On the other hand, when the reception intensity is less than the specific value (No in step S103), the control unit 201 shifts to the passive mode by, for example, resetting the flag managed in the memory unit 202 (step S105).

Next, the control unit 201 generates the control signal s12 of, for example, the high level which turns on the second switch SW2 and supplies it to the second switch SW2 to turn on a disconnection switch, thereby electrically connecting the drive coil driving unit 222 and the drive coils 223a and 223b (step S106) and starting the operation of the signal generating unit 221 (step S107). As a result, a drive signal of the frequency almost equal to the resonance frequency F0 is output from the signal generating unit 221. The drive signal output from the signal generating unit 221 is amplified in the drive coil driving unit 222 and, after that, the amplified signal is input to the drive coils 223a and 223b via the second switch SW2 which is in the on state. On the other hand, the drive coils 223a and 223b generate the drive magnetic field having a frequency almost equal to the resonance frequency F0 in the detection space K in accordance with the input drive signal. After step S107, the control unit 201 finishes the mode switching process.

By executing the mode switching process as described above, in the embodiment, according to the signal intensity of the detection signal detected by the signal processing unit 211, that is, the battery remaining amount or the operation mode of the capsule medical device 10, the operation mode of the external apparatus 200 can be switched.

Position Detecting Process

Next, the position detecting process according to the embodiment will be described in detail with reference to the drawings. As described above, the position detecting process according to the embodiment includes the position detecting process in the passive mode and the position detecting process in the active mode.

Figure 7:
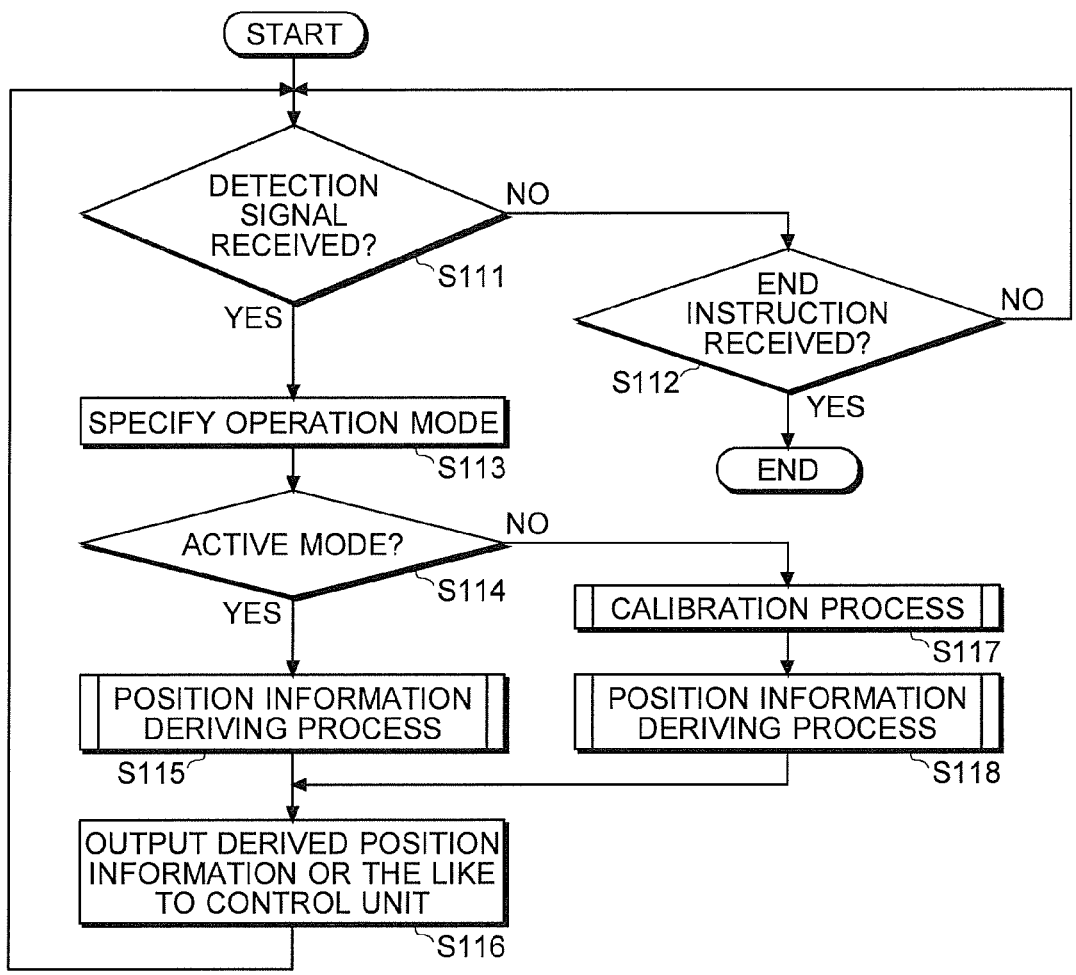
FIG. 7 is a flowchart showing outline of a position detecting process according to any of the first to third embodiments of the invention.

FIG. 7 is a flowchart showing outline of the position detecting process according to the embodiment. The position detecting process is executed in the position calculating unit 212. As shown in FIG. 7, in the position detecting process, first, the position calculating unit 212 periodically determines whether a detection signal subjected to processes such as amplification, band limitation, AD conversion, and FFT is received from the signal processing unit 211 (step S111). The position calculating unit 212 periodically determines, for example, whether an end instruction is supplied from the control unit 201 (step S112). Therefore, when no detection signal is received (No in step S111) and the end instruction is not received (No in step S112), the position calculating unit 212 returns to step S111. In the case where the end instruction is received (Yes in step S112), the position calculating unit 212 finishes the process. To the signal processing unit 211, the detection signal detected in each of the plurality of sense coils 213 is periodically supplied. The signal processing unit 211 processes each of the detection signals supplied from the sense coils 213, associates the processed detection signals with the sense coils 213, and supplies them to the position calculating unit 212. In the case where it is determined, for example, in step S103 in FIG. 6 that the end instruction from the operator is received, the control unit 201 enters the end instruction to the position calculating unit 212.

In the case where it is determined in step S111 that the detection signal is received from the signal processing unit 211 (Yes in step S111), the position calculating unit 212 specifies whether the present operation mode is the active mode or the passive mode (step S113). The operation mode may be specified, for example, by directly referring to the memory unit 202 to check the flag managing the operation mode by the position calculating unit 212, or by referring to the flag via the control unit 201.

Next, the position calculating unit 212 determines whether the present operation mode is the active mode (step S114). When the present operation mode is the active mode (Yes in step S114), the position calculating unit 212 executes a position information deriving process using the detection signal received from the signal processing unit 211 (step S115). The position information deriving process in step S115 will be described in detail later.

Subsequently, the position calculating unit 212 supplies the derived position information or the like to the control unit 201 (step S116) and, after that, returns to step S111. The control unit 201 to which the position information or the like is supplied displays the present position and direction of the capsule medical device 10 on the display unit 204 by using the position information or the like. At this time, the in-vivo information such as a most-recent in-vivo image received from the capsule medical device 10 may be displayed on the display unit 204 together with the present position and direction of the capsule medical device 10. The position information or the like which is output in step S115 may be stored in the memory unit 202 together with the most-recent in-vivo information and information such as time at which the information is derived.

On the other hand, in the case where the present operation mode is the passive mode as a result of determination in step S114 (No in step S114), the position calculating unit 212 executes the calibration process on the detection signal received from the signal processing unit 211 (step S117). The calibration process in step S117 will be described in detail later.

Next, the position calculating unit 212 executes the position information deriving process using the detection signal from which the drive coil unnecessary magnetic field information is removed by the calibration process (step S118), after that, moves to step S116 where the derived position information or the like is supplied to the control unit 201 (step S116), and returns to step S111. The position information deriving process in step S118 will be described in detail later together with the position information deriving process in step S115.

By executing the position detecting process as described above, in the embodiment, accurate position information or the like can be derived according to the operation mode.

Calibration Process

Next, the calibration process in step S117 in FIG. 7 will be described in detail. In the calibration process in step S117, a process of removing the drive magnetic field information included in the detection signal output from the signal processing unit 211 is executed. Magnetic field information B_dt (vector) indicated by the detection signal output from the sense coil 213 includes, as described above and as expressed by the following Equation (1), drive magnetic field information B_dr (vector) and resonance magnetic field information B_reso (vector). Therefore, the resonance magnetic field information B_reso (vector) can be obtained by subtracting the drive magnetic field information B_dr (vector) from the magnetic field information B_dr (vector) by vector operation as shown by the following Equation (2) (calibration process). Although unnecessary magnetic field information is also included in the detection signal, for simplicity of explanation, the unnecessary magnetic field information is ignored here.

$$\vec{B}\_dt = \vec{B}\_dr + \vec{B}\_reso \tag{1}$$

$$\vec{B}\_reso = \vec{B}\_dt + \vec{B}\_dr \tag{2}$$

Figure 8:
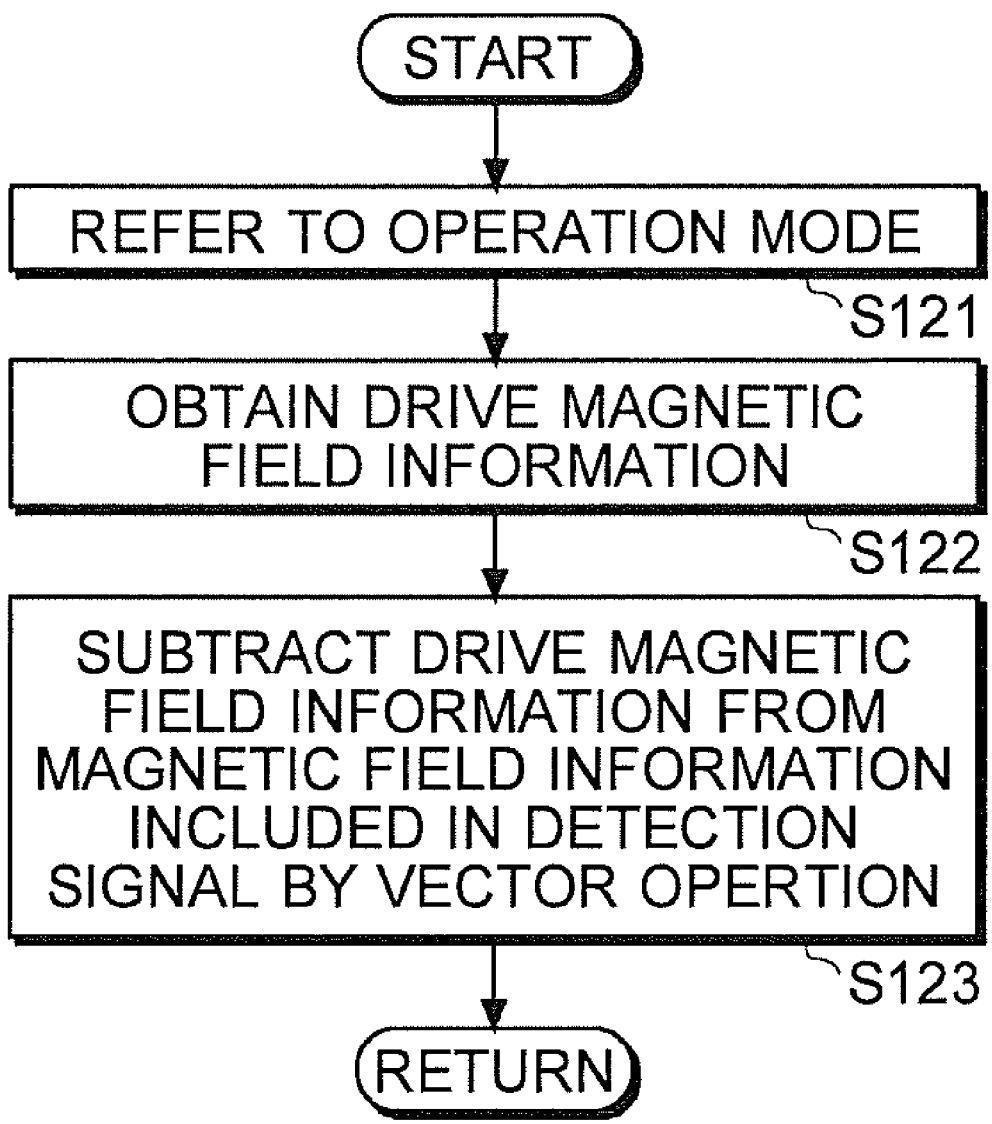
FIG. 8 is a flowchart showing outline of a calibration process according to any of the first to third embodiments of the invention.

In the embodiment, by using an operation flow as shown in FIG. 8, the calibration process of removing the drive magnetic field information from the detection signal is executed. FIG. 8 is a flowchart showing outline of the calibration process according to the embodiment.

As shown in FIG. 8, in the calibration process, first, the position calculating unit 212 refers to the operation mode specified in step S113 in FIG. 7 (step S121) and obtains the drive magnetic field information (which will be also called calibration information) B_dr (vector) according to the operation mode (step S122). Next, the position calculating unit 212 subtracts the drive magnetic field information B_dr (vector) obtained in step S122 from the magnetic field information B_dt (vector) included in the detection signal received in step S111 in FIG. 7 and, after that, returns to step S117 in FIG. 7.

By executing the calibration process as described above, in the embodiment, the drive magnetic field information included as unnecessary magnetic field information in the detection signal can be removed. Also in the case where the present operation mode is the active mode (Yes in step S114), a calibration process similar to the operation shown in FIG. 8 may be executed. In this case, the calibration information used for the removal is a vector of substantially "0".

The drive magnetic field information B_dr (vector) used in the calibration process can be calculated by, for example, generating the drive magnetic field in the detection space K by driving the drive coils 223a and 223b in a state where the capsule medical device 10 (that is, the LC resonance circuit 111) is not introduced in the detection space K, and driving the signal processing unit 211 and the position calculating unit 212 in this state. The calculated drive magnetic field information B_dr (vector) is managed in, for example, the memory unit 202 or the like. Therefore, the position calculating unit 212 calculates the resonance magnetic field information B_reso (vector) by obtaining the drive magnetic field information B_dr (vector) by properly referring to the memory unit 202 or the like and subtracting the obtained drive magnetic field information B_dr (vector) from the magnetic field information B_dt (vector) included in the detection signal by vector operation (step S123).

Position Information Deriving Process

Next, the position information deriving process in steps S115 and S118 in FIG. 7 will be described in detail. Since the principle of the position information deriving process in step S115 and that in step S118 are similar to each other, in the following description, attention is paid to the position information deriving process in step S115.

In the position information deriving process according to the embodiment, from the resonance magnetic field information obtained by removing the unnecessary magnetic field information included in the detection signal, accurate position information or the like is derived. For example, in the position information deriving process in step S115, that is, in the position information deriving process in the active mode, correction of removing guidance coil unnecessary magnetic field information included as unnecessary magnetic field information in the magnetic field information is executed.

At the time of deriving the position information or the like, each of the sense coils 213 disposed close to the detection space K detects a detection signal of a voltage proportional to a magnetic flux passing through the sense coil 213 itself. Therefore, from the detection signal supplied from the sense coil 213 to the position calculating unit 212 via the signal processing unit 211, the magnetic flux passing through the sense coil 213 can be obtained. In the following description, the magnetic flux obtained from the detection signal supplied from an arbitrary sense coil 213 to the position calculating unit 212 via the signal processing unit 211 will be called a magnetic flux Bdi.

When it is assumed that the resonance magnetic field from the LC resonance circuit 111 in the capsule medical device 10 is a resonance magnetic field from a magnetic dipole, the position information or the like of the LC resonance circuit 111 (that is, the capsule medical device 10) can be calculated by the following method. In the following method, a magnetic moment of the magnetic dipole (the LC resonance circuit 111), the position coordinates of the magnetic dipole, and a position vector of a place where the magnetic field is desired to be calculated (the position of an arbitrary sense coil 213) are set as shown in the following Equations (3), (4), and (5). Consequently, a position vector for the magnetic dipole, of the place where the magnetic field is desired to be calculated and the magnetic field intensity in the place can be expressed by the following Equations (6) and (7).

$$\text{Magnetic moment of magnetic dipole: } \vec{M}[Mx, My, Mz] \quad (3)$$

$$\text{Position coordinates of magnetic dipole: } [x, y, z] \quad (4)$$

$$\text{Position vector of place where magnetic field is desired to be calculated: } \vec{r}_{si}[xi, yi, zi] \quad (5)$$

Position vector for magnetic dipole, of place where magnetic field is desired to be calculated:

$$\vec{r}_i[xi-x, yi-y, zi-z] \quad (6)$$

Magnetic field intensity in place where magnetic field is desired to be calculated:

$$\vec{B}i = \frac{1}{4\pi}\left(\frac{3(\vec{M}\cdot\vec{r}_i)}{r_i^5}\vec{r}_i - \frac{\vec{M}}{r_i^3}\right) \quad (7)$$

By expressing them as described above, optimization calculation of minimizing an evaluation function shown by the following Equation (8) can be executed.

$$\sum_{i=1}^{n}\left(\vec{B}_{di} - \vec{B}_i(\vec{p})\right)^2 \quad (8)$$

where $\vec{p} = (x, y, z, Mx, My, Mz)$ is a vector made by parameters of magnetic dipole Since the evaluation function shown in Equation (8) is obtained in each of the plurality of sense coils 213, a vector made by a parameter of the magnetic dipole can be presumed by using a plurality of evaluation functions.

In the detection signal processed in step S115, not only the resonance magnetic field information but also the guidance coil unnecessary magnetic field information is also included. The guidance coils 233x to 233z and 234x to 234z (hereinbelow, the reference numeral for an arbitrary guidance coil will be 233) as the source of generating the guidance coil unnecessary magnetic field are usually connected to the drive coil driving unit 222 of low impedance. Consequently, when the resonance magnetic field passes through the guidance coil 233, the guidance coil 233 is excited by the resonance magnetic field, and a current determined by the impedance of the drive coil 223a or 223b flows. By the current, the magnetic field (guidance coil unnecessary magnetic field) having a phase cancelling out the magnetic flux which passed through the drive coil is generated.

When the position and direction of the guidance coil 233 are determined, the guidance coil unnecessary magnetic field generated as described above can be obtained. That is, when the position and direction of the guidance coil 233 are fixed, the magnetic flux density (refer to the following Equation (9)) passing through a point in an open plane of the guidance coil 233 can be obtained.

magnetic flux density: $\vec{B}g(\vec{p})$ (9)

The magnetic flux density shown in Equation (9) is derived from an electromotive force generated in the guidance coil 233. In calculation of the magnetic flux density, a plurality of calculation points are set, and an average value is obtained. An average value of the magnetic flux densities can be expressed by the following Equation (10).

average value of magnetic flux density:

$$\vec{B}g\_mean(\vec{p}) = \frac{1}{N}\sum_{k=1}^{N}\vec{B}gk(\vec{p}) \quad (10)$$

The electromotive force generated in the guidance coil 233 by the resonance magnetic field is proportional to the average value of the magnetic flux densities expressed by Equation (10) in the number of turns, area, and angular frequency of the guidance coil 233. Therefore, the current flowing in the guidance coil 233 can be obtained by dividing the electromotive force by the impedance of the guidance coil 233. That is, the current flowing in the guidance coil 233 by the resonance magnetic field can be also expressed by the function of the vector made by the parameter of the magnetic dipole (LC resonance circuit 111) as shown by the following Equation (11).

current flowing in guidance coil: $Ic(\vec{p})$ (11)

However, the guidance coil 233 is much larger than the LC resonance circuit 111. Consequently, the guidance coil 233 cannot be handled as a magnetic dipole. In the embodiment, the guidance coil 233 is divided in a plurality of current vectors and the Biot-Savart law is applied. By performing addition only by the number of divisions, the current can be obtained.

By setting the position vector of a current element, a current vector, and the position vector of coordinates where a magnetic field is desired to be calculated as shown by the following Equations (12), (13), and (14), the guidance unnecessary magnetic field information (magnetic field intensity (vector)) included in the detection signal detected by the sense coil 213 can be expressed by the following Equation (15).

position vector of current element: $\vec{r}_c$ (12)

current vector: $\vec{d}_c$ (13)

position vector of coordinate where magnetic field is desired to be calculated: $\vec{r}_{si}$ (14)

guidance coil unnecessary magnetic field information:

$$\vec{B}_{ci}(\vec{p}) = \oint \mu_0 \frac{I(\vec{p})d\vec{c} \times (\vec{r}_{si} - \vec{r}_c)}{4\pi|\vec{r}_{si} - \vec{r}_c|^3} \quad (15)$$

The distribution shape of the guidance unnecessary magnetic field information included in the detection signal obtained in each of the sense coils 213 is determined when the position relative to the guidance coil 233 is determined. By preliminarily calculating current $I_c$ flowing in the guidance coil 233 as 1 and holding and managing it as a look-up table (LUT) in the memory unit 202 or the like, calculation can be simplified.

Since the magnetic field information included in the detection signal obtained by the sense coil 213 and the resonance magnetic field B(p) generated by the magnetic dipole (LC resonance circuit 111) cancel out each other, a total value of the magnetic field $B_c(p)$ is obtained. Therefore, the evaluation function in the position derivation can be expressed by the following Equation (16).

$$\text{evaluation function } \sum_{i=1}^{n}(\vec{B}_{di} - \vec{B}_i(\vec{p}) - \vec{B}_{ci}(\vec{p}))^2 \quad (16)$$

Figure 9:
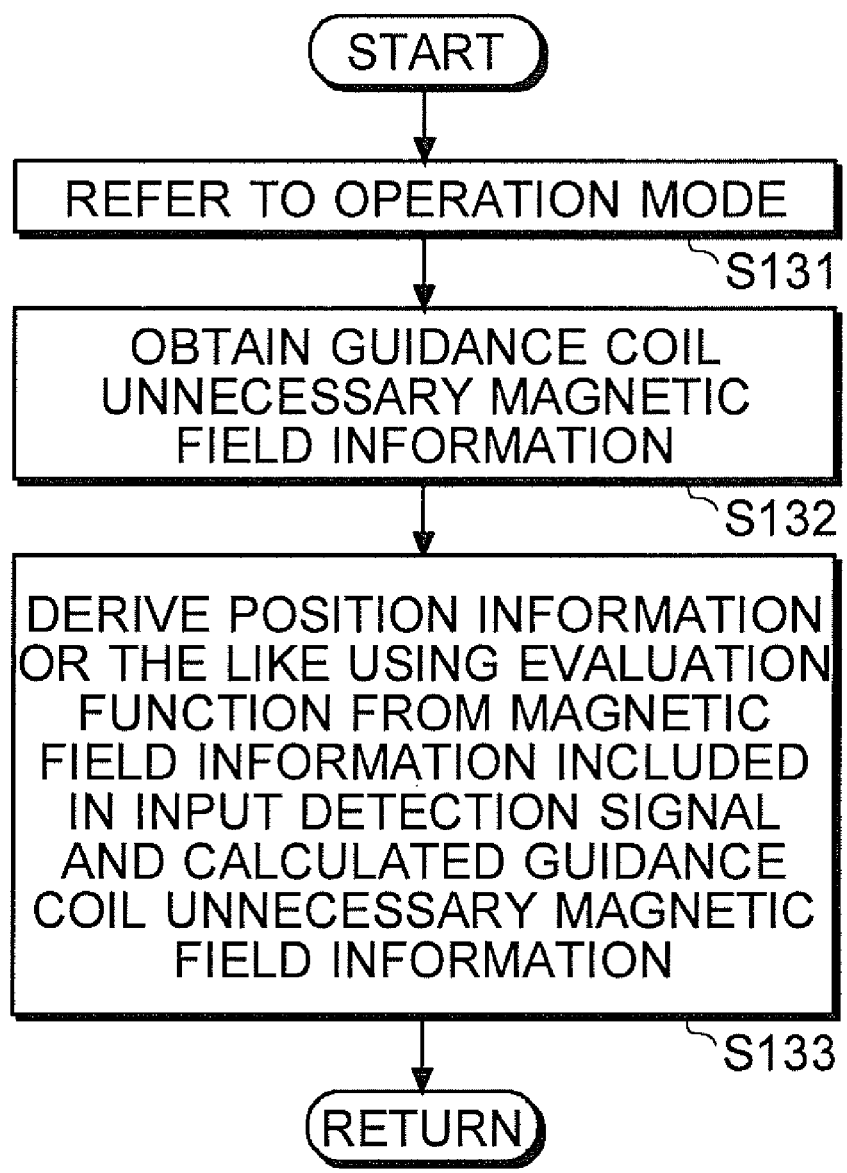
FIG. 9 is a flowchart showing a position information deriving process according to any of the first to third embodiments of the invention.

Based on the principle as described above, in the embodiment, the position information or the like is derived from the detection signal by using the operation flow as shown in FIG. 9. FIG. 9 is a flowchart showing outline of the position information deriving process according to the embodiment.

As shown in FIG. 9, in the position information deriving process, first, the position calculating unit 212 refers to the operation mode specified in step S113 in FIG. 7 (step S131) and, subsequently, refers to the LUT held in the memory unit 202 or the like directly or via the control unit 201, thereby obtaining the guidance coil unnecessary magnetic field information in each of the sense coils 213 according to the operation mode (active mode) (step S132). Next, the position calculating unit 212 derives the position information or the like from the obtained guidance coil unnecessary magnetic field information (and the drive coil unnecessary magnetic field information) and the magnetic field information included in the detection signal (or the magnetic field information subjected to the calibration process) by using the evaluation function shown in the above Equation (16) (step S133). After that, the position calculating unit 212 returns to step S115 in FIG. 7.

As described above, by deriving the position information or the like while cancelling the unnecessary magnetic field information, in the embodiment, the accurate position information or the like can be derived. In the passive mode, not only the guidance coil unnecessary magnetic field information, but also the drive coil unnecessary magnetic field information is included as the unnecessary magnetic field information in the detection signal. Therefore, for example, in the position information deriving process in step S118, the position information or the like is derived in consideration of not only the guidance coil unnecessary magnetic field information but also the drive coil unnecessary magnetic field information. Since the principle of the process of cancelling the drive coil unnecessary magnetic field information and that of the process of cancelling the guidance coil are similar to each other, the detailed description will not be given here.

By performing the calibration process (refer to FIG. 8) and/or the position information deriving process (refer to FIG. 9) as the position detecting process described with reference to FIGS. 7 to 9, the present position information may be each time. Alternatively, by preliminarily calculating the position information or the like according to the operation mode and the detection signal and holding and managing it as the LUT, the present position information or the like may be specified by properly referring to the LUT in accordance with the present operation mode and the detection signal at the time of detection.

Averaging Process

To further improve the precision of the position information or the like derived by the position detecting process shown in FIG. 7, a process of averaging a plurality of pieces of position information or the like (hereinbelow, called averaging process) may be executed. The averaging process is executed, for example, in the control unit 201. That is, the control unit 201 also functions as an averaging process unit for averaging a plurality of pieces of position information or the like. In the following, the averaging process according to the embodiment will be described in detail with reference to FIG. 10.

Figure 10:
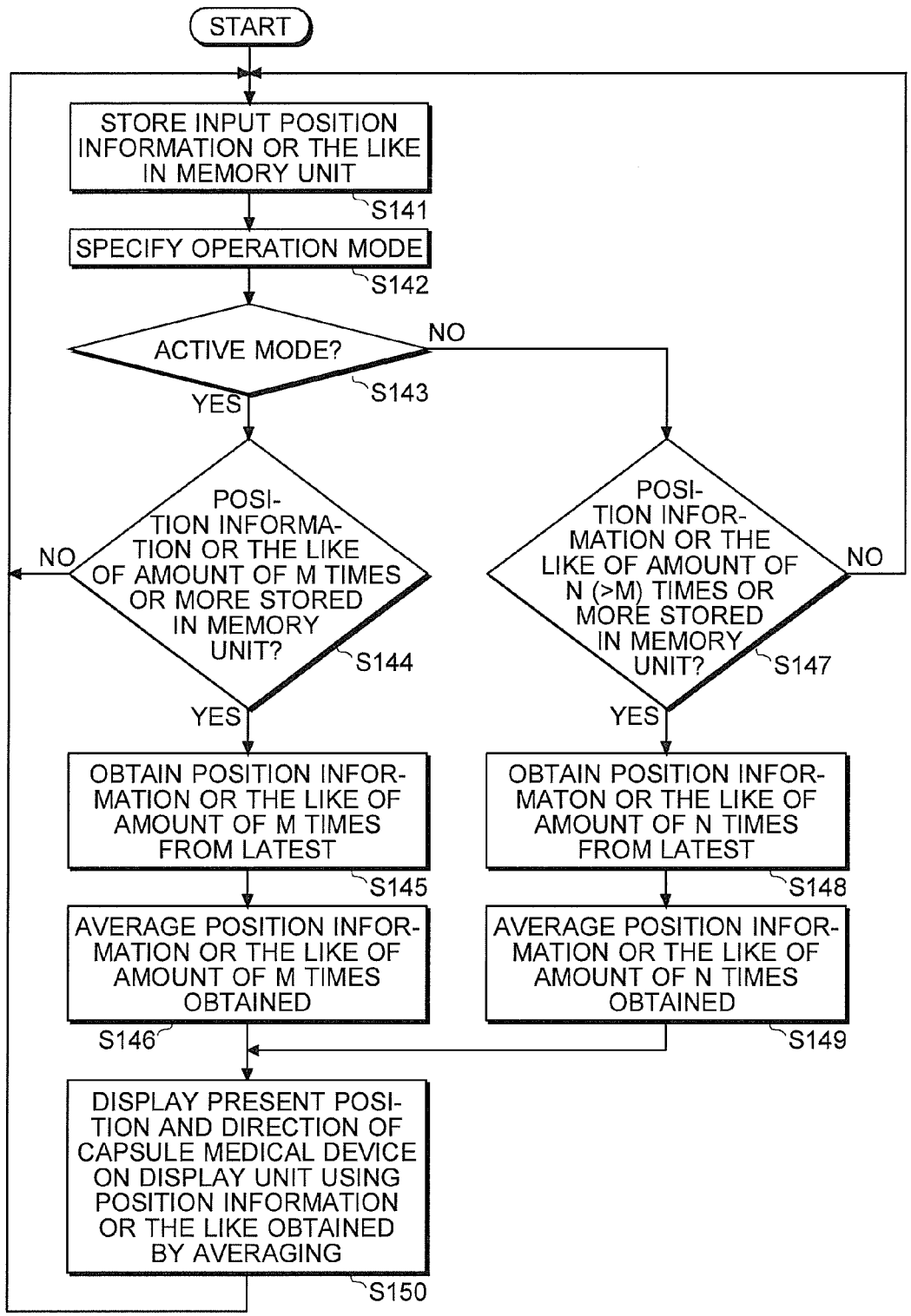
FIG. 10 is a flowchart showing outline of an averaging process according to any of the first to third embodiments of the invention.

FIG. 10 is a flowchart showing outline of the averaging process according to the embodiment. As shown in FIG. 10, in the averaging process, first, when the position information or the like is supplied from the position calculating unit 212, the control unit 201 temporarily stores it in the memory unit 202 (step S141). Subsequently, the control unit 201 specifies the present operation mode (step S142). In the case where the present operation mode is the active mode (Yes in step S143), whether the position information or the like of M times or more is stored in the memory unit 202 is determined (step S144). M is a positive integer.

When it is determined in step S144 that the position information or the like of M times or more is stored in the memory unit 202 (Yes in step S144), the control unit 201 obtains position information or the like of M times by counting it from the latest one from the memory unit 202 (step S145) and averages it (step S146). As a result, the position information or the like whose precision is improved by being averaged is generated. On the other hand, when it is determined in step S144 that the position information or the like of M times is not stored in the memory unit 202 (No in step S144), the control unit 201 returns to step S141.

In the case where the present operation mode specified in step S142 is the passive mode (No in step S143), the control unit 201 determines whether position information or the like of N times or more is stored in the memory unit 202 (step S147). N is a positive integer larger than M. The reason why N is set to be larger than M will be described later.

In the case where it is determined in step S147 that the position information or the like of N times or more is stored in the memory unit 202 (Yes in step S147), the control unit 201 obtains position information or the like of N times by counting it from the latest one from the memory unit 202 (step S148) and averages it (step S149). As a result, the position information or the like whose precision is improved by being averaged is generated. On the other hand, when it is determined in step S147 that the position information or the like of N times is not stored in the memory unit 202 (No in step S147), the control unit 201 returns to step S141.

After that, the control unit 201 displays the present position and direction of the capsule medical device 10 on the display unit 204 by using the averaged position information or the like generated in step S146 or S149 (step S150) and, then, returns to step S141. In step S150, the in-vivo information such as the latest in-vivo image received from the capsule medical device 10 may be displayed on the display unit 204 together with the present position and direction of the capsule medical device 10.

There is a case that the precision of the position information or the like derived in the passive mode is lower than that of the position information or the like derived in the active mode. In the embodiment, the parameter N used for averaging in the passive mode is set to a value larger than the parameter M used for averaging in the active mode. For example, M is set to 1, and N is set to 10. That is, the control unit 201 functioning as the averaging processor may change the parameter for the position information or the like to be averaged between the case where the second switch SW2 is on and the case where the second switch SW2 is off. By the operation, the position detection precision in the active mode and that in the passive mode can be made almost the same.

Guidance Process

Next, the guidance process according to the embodiment will be described in detail with reference to the drawings. In the following description, for simplicity, the case where the operator enters only one of the movement instruction and the end instruction from the operation unit 203 will be described as an example. The invention, however, is not limited to the case. Another operation instruction such as the image capturing instruction as described above may be entered from the operation unit 203.

Figure 11:
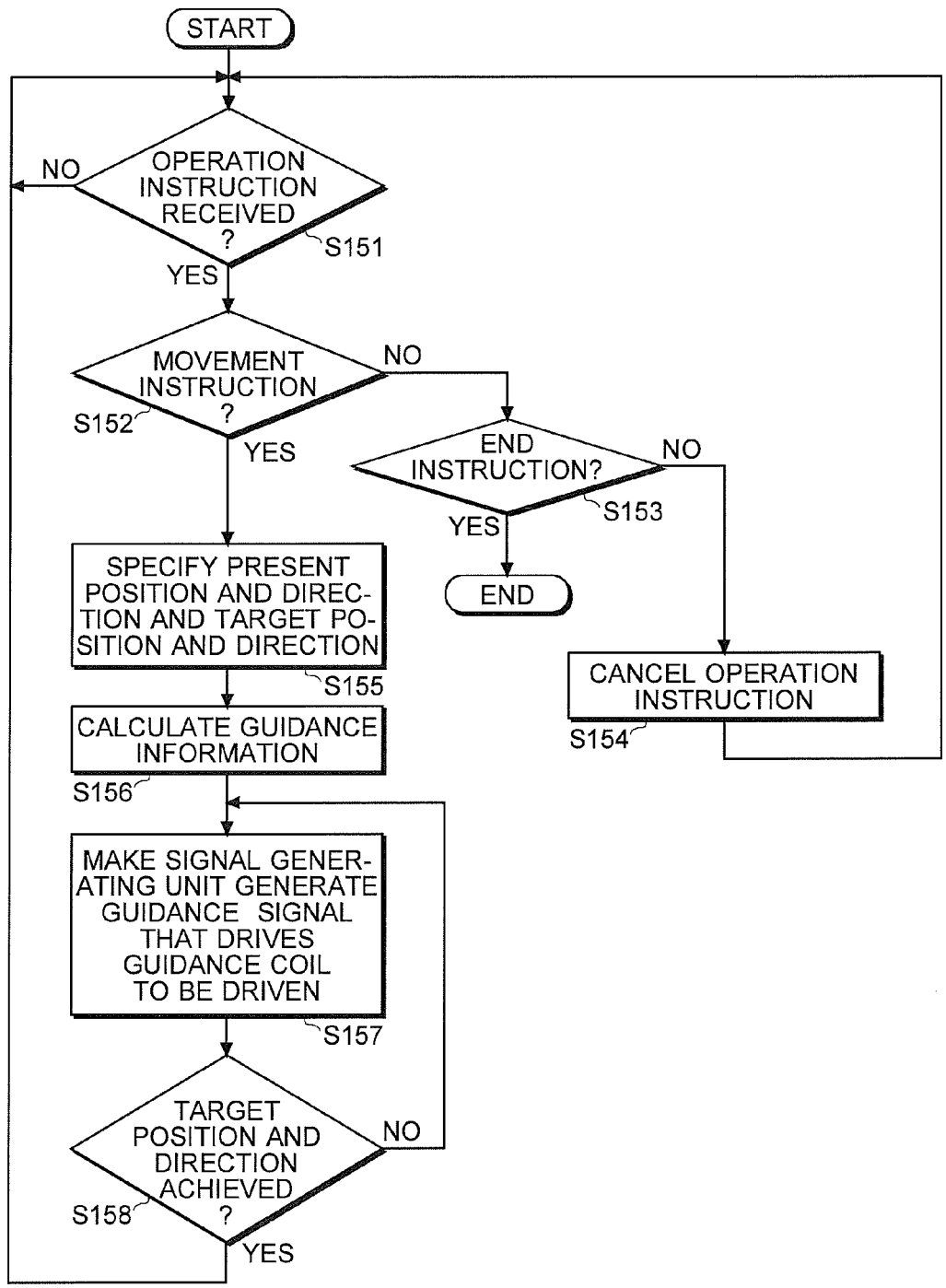
FIG. 11 is a flowchart showing outline of a guidance process according to the first embodiment of the invention.

FIG. 11 is a flowchart showing outline of the guidance process according to the embodiment. As shown in FIG. 11, in the guidance process, first, the control unit 201 monitors whether the operation instruction is entered by the operator using the operation unit 203 (step S151). In the case where the operation instruction is entered (Yes in step S151), the control unit 201 determines whether the operation instruction is the movement instruction (step S152). With respect to the operation, the control unit 201 waits until the operation instruction is entered (No in step S151). When it is determined in step S152 that the input operation instruction is not the movement instruction (No in step S152), the control unit 201 determines whether the input operation instruction is the end instruction (step S153). When it is the end instruction (Yes in step S153), the control unit 201 finishes the guidance process. On the other hand, when the input operation instruction is not the end instruction (No in step S153), the control unit 201 cancels the input operation instruction (step S154) and returns to step S151.

When it is determined in step S152 that the input operation instruction is the movement instruction (Yes in step S152), the control unit 201 refers to the memory unit 202 to specify the present position and direction of the capsule medical device 10, also specifies the input target position and direction (step S155) and, using them, calculates information of the guidance magnetic field (guidance information) to be given to the magnetic field generator (permanent magnet) 12 mounted on the capsule medical device 10 (step S156).

After that, the control unit 201 makes the signal generating unit 231 of the capsule guidance unit 230 generate a guidance signal for generating the guidance magnetic field calculated in step S156 (step S157). The control unit 201 determines whether the capsule medical device 10 could achieve the target position and direction (step S158) and continues the operation of step S157 until it can achieve it (No in step S158). In the case where it can achieve (Yes in step S158), the control unit 201 returns to step S151.

By the operation as described above, the guidance signal to be given to the guidance coil 233 is output from the signal generating unit 231. The guidance signal output from the signal generating unit 231 is current-amplified by the guidance coil driving unit 232 and the amplified signal is supplied to the guidance coil 233. According to the input guidance signal, the guidance coil 233 generates a guidance magnetic field for guiding the capsule medical device 10 to the target position and direction in the detection space K. After step S158, the control unit 201 returns to step S151. The process is finished by, for example, an interrupt process.

As described above, according to the embodiment, by switching the first switch SW1 on the basis of the voltage level of the power source voltage VCC supplied from the capsule internal power source 17 in the capsule medical device 10 as a body-insertable apparatus, the operation mode can be switched between the active mode in which the LC resonance circuit 111 spontaneously emits the resonance magnetic field and the passive mode in which the LC resonance circuit 111 receives the external magnetic field (drive magnetic field) and emits the resonance magnetic field. By switching the second switch SW2 in accordance with the signal intensity (in other words, intensity of the resonance magnetic field) of the detection signal detected by the sense coil 213 in the external apparatus 200, the operation mode can be switched between the passive mode of making the drive coils 223a and 223b emit the drive magnetic field and the active mode of emitting no drive magnetic field. In such a manner, the position detecting magnetic guidance system 1 capable of detecting the position or the like of the capsule medical device 10 while switching the active and passive modes in accordance with the situation can be realized.

In the embodiment, the case that when the capsule medical device 10 shifts to the passive mode at the turn-off of the first switch SW1, the shift is automatically detected in the external apparatus 200 and the operation mode of the external apparatus 200 also shifts to the passive mode has been described as an example. The invention, however, is not limited to the case. For example, the operator may switch the operation mode of the external apparatus 200 using the operation unit 203. For example, when the present position and direction of the capsule medical device 10 are not displayed on the display unit 204, the operator enters an instruction of switching the operation mode to the external apparatus 200 using the operation unit 203. The external apparatus 200 turns on the second switch SW2 and supplies a drive signal to the drive coils 223a and 223b in accordance with the operation, thereby generating the drive magnetic field in the detection space K. By detecting an excitation magnetic field emitted from the capsule medical device 10 by the drive magnetic field, the present position and direction of the capsule medical device 10 are obtained and displayed on the display unit 204.

First Modification

Figure 12:
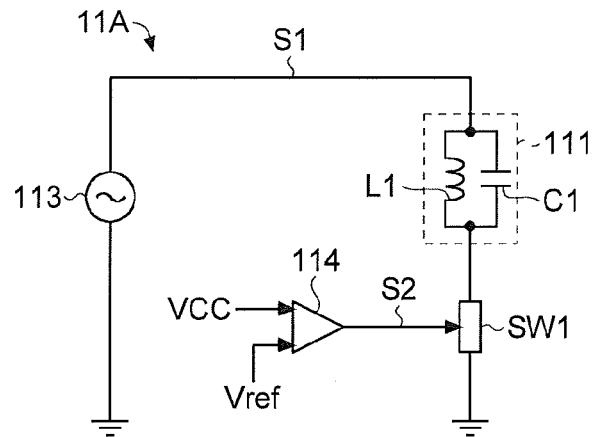
FIG. 12 is a diagram showing a schematic configuration of a resonance magnetic field generator according to a first modification of the first embodiment of the invention.
Figure 13:
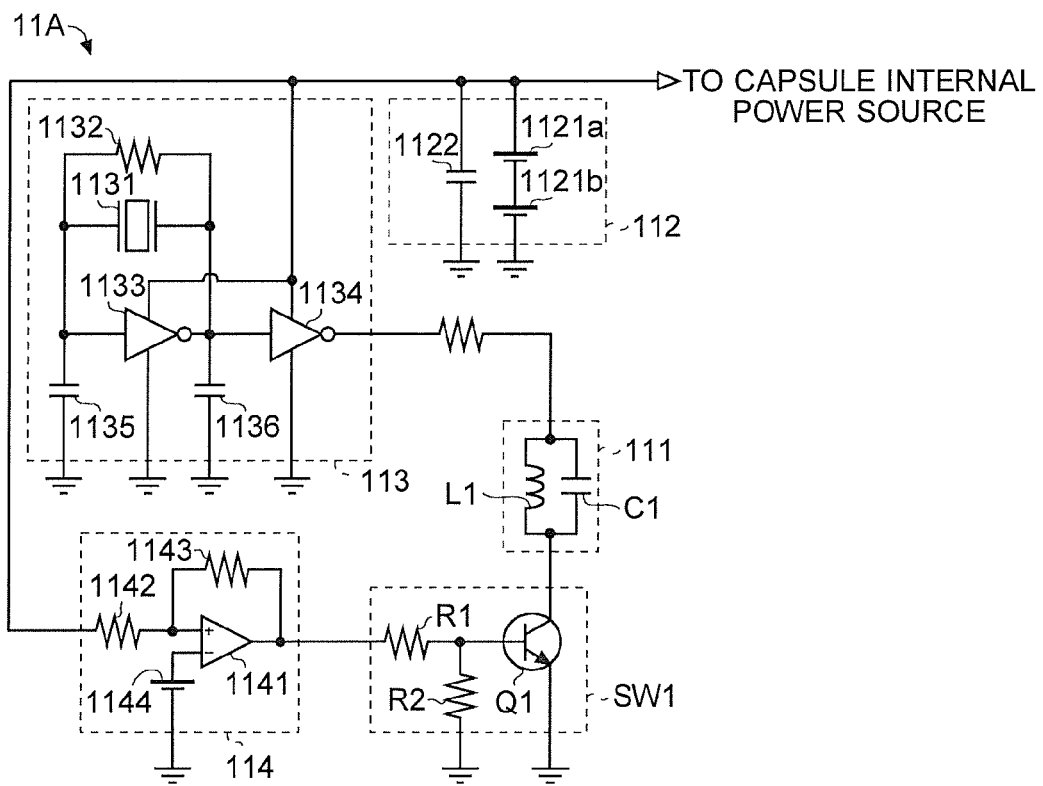
FIG. 13 is a diagram showing a circuit configuration example of the resonance magnetic field generator according to the first modification of the first embodiment of the invention.

The resonance magnetic field generator 11 in the capsule medical device 10 according to the embodiment can have a configuration as shown in FIGS. 12 and 13. The configuration of a resonance magnetic field generator 11A shown in FIGS. 12 and 13 will be described as a first modification of the first embodiment of the invention.

As obvious from comparison between FIGS. 4 and 12 and between FIGS. 5 and 13, the resonance magnetic field generator 11A according to the first modification has a configuration that the first switch SW1 is provided between the LC resonance circuit 111 and the ground line, not between the oscillation circuit 113 and the LC resonance circuit 111.

It is sufficient for the first switch SW1 according to the embodiment to disconnect at least one place in the portion from the oscillation circuit 113 as a guidance signal supply source to the ground line. With such a simple configuration, supply of the guidance signal to the LC resonance circuit 111 can be stopped and the operation mode of the capsule medical device 10 can be switched. Since the other configuration and operation are similar to those of the first embodiment, the detailed description will not be repeated here.

Second Modification

Figure 14:
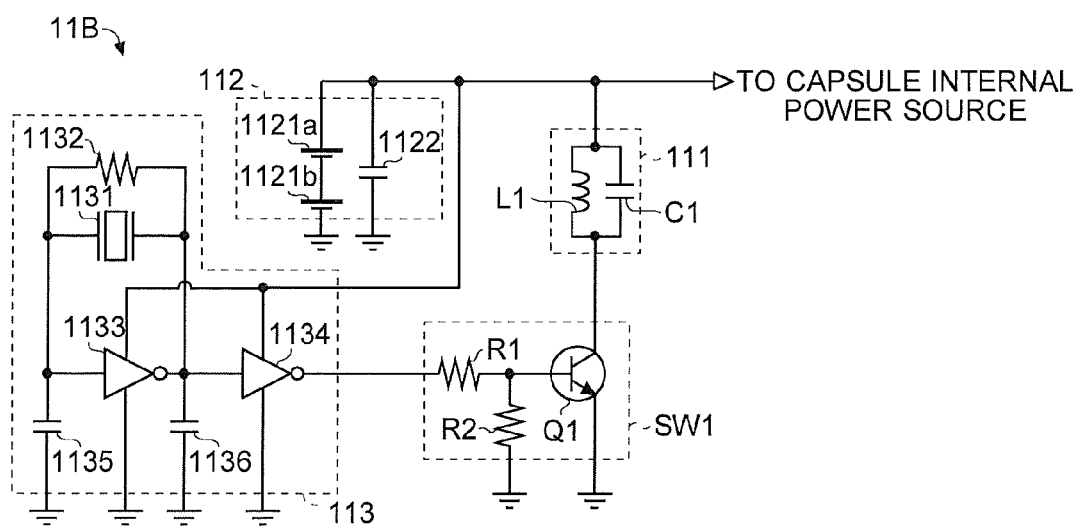
FIG. 14 is a diagram showing a circuit configuration example of a resonance magnetic field generator according to a second modification of the first embodiment of the invention.

Further, the resonance magnetic field generator 11 in the capsule medical device 10 according to the embodiment can have a configuration as shown in FIG. 14. The configuration of a resonance magnetic field generator 11B shown in FIG. 14 will be described as a second modification of the first embodiment of the invention.

As obvious from comparison between FIGS. 5 and 14, the resonance magnetic field generator 11B according to the second modification has a configuration that the drive circuit 114 (refer to FIG. 5) is not provided.

In the resonance magnetic field generator 11B, using the base-emitter voltage of the transistor Q1 in the first switch SW1, the switching between the active mode and the passive mode is performed. Therefore, when the voltage level of the power source voltage VCC supplied from the capsule internal power source 17 in the capsule medical device 10 drops, the voltage level of the guidance signal output from the oscillation circuit 113 which oscillates according to the application voltage drops, so that the first switch SW1 cannot be turned on. As a result, the transistor Q1 remains off. Consequently, in a manner similar to the first embodiment, the active mode and the passive mode can be switched according to the voltage level of the power source voltage VCC supplied from the capsule internal power source 17. Since the other configuration and operation are similar to those of the first embodiment, the detailed description will not be repeated here.

Second Embodiment

The configuration and operation of a position detecting magnetic guidance system according to a second embodiment of the invention will be described in detail with reference to the drawings. The position detecting magnetic guidance system according to the embodiment can use a configuration similar to that of the position detecting magnetic guidance system 1 according to the first embodiment. In the second embodiment, the resonance magnetic field generator 11 of the capsule medical device 10 is replaced with a resonance magnetic field generator 21.

Configuration

Figure 15:
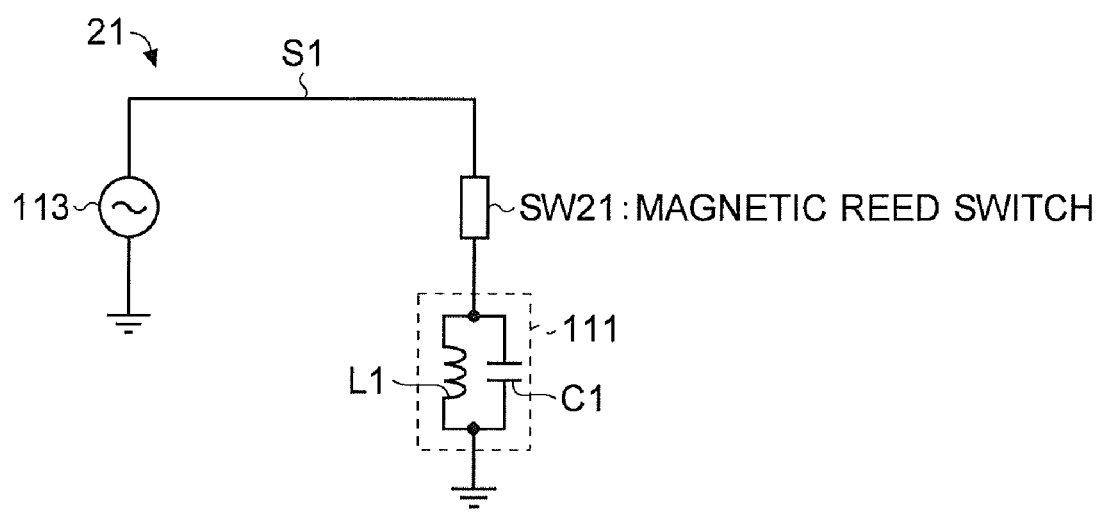
FIG. 15 is a diagram showing a schematic configuration of a resonance magnetic field generator according to a second embodiment of the invention.

FIG. 15 shows a schematic configuration of the resonance magnetic field generator 21 according to the embodiment. As obvious from comparison between FIGS. 15 and 4, in the resonance magnetic field generator 21 according to the embodiment, the first switch SW1 (refer to FIG. 4) in the resonance magnetic field generator 11 of the first embodiment is replaced with a magnetic reed switch SW21 (refer to FIG. 15).

The magnetic reed switch SW21 is turned on when a magnetic field having intensity above a certain level is applied from the outside, and maintains the off state when the intensity of the magnetic field on the outside is less than the certain level. In the embodiment, by applying the magnetic field to turn on the magnetic reed switch SW21 (hereinbelow, called mode switching magnetic field) to the capsule medical device 10 introduced in the detection space K by using the external apparatus 200, the operation mode of the capsule medical device 10 is switched from the outside.

The mode switching magnetic field can be emitted from the guidance coil 233 by, for example, controlling the capsule guidance unit 230. At this time, the magnetic field having an intensity which is sufficiently lower than a level at which the position and direction of the capsule medical device 10 can be guided, and at which the magnetic reed switch SW21 can be turned on is emitted as the mode switching magnetic field from the guidance coil 233. The mode switching magnetic field is emitted, for example, when the control unit 201 makes the signal generating unit 231 of the capsule guidance unit 230 emit a mode switching magnetic field (hereinbelow, mode switching signal) to the guidance coil 233, current-amplifies the signal in the guidance coil driving unit 232, and properly supplies the amplified signal to the guidance coil 233. As described above, the guidance coil 233 and the guidance coil driving unit 232 for driving the guidance coil 233 according to the embodiment also function as a switching coil for generating the mode switching magnetic field in the detection space K and a switching coil driving unit for driving the switching coil. The invention is not limited to the configuration. The mode switching magnetic field may be generated by using the drive coil 223a and/or the drive coil 223b or by providing a dedicated magnetic field emitter and a coil.

Since the other configuration is similar to that of the first embodiment of the invention, the detailed description will not be repeated.

Third Embodiment

The configuration and operation of a position detecting magnetic guidance system according to a third embodiment of the invention will be described in detail with reference to the drawings. The position detecting magnetic guidance system according to the embodiment can use a configuration similar to that of the position detecting magnetic guidance system 1 according to the first embodiment. In the third embodiment, the capsule medical device 10 is replaced with a capsule medical device 30 shown in FIG. 16.

Configuration

Figure 16:
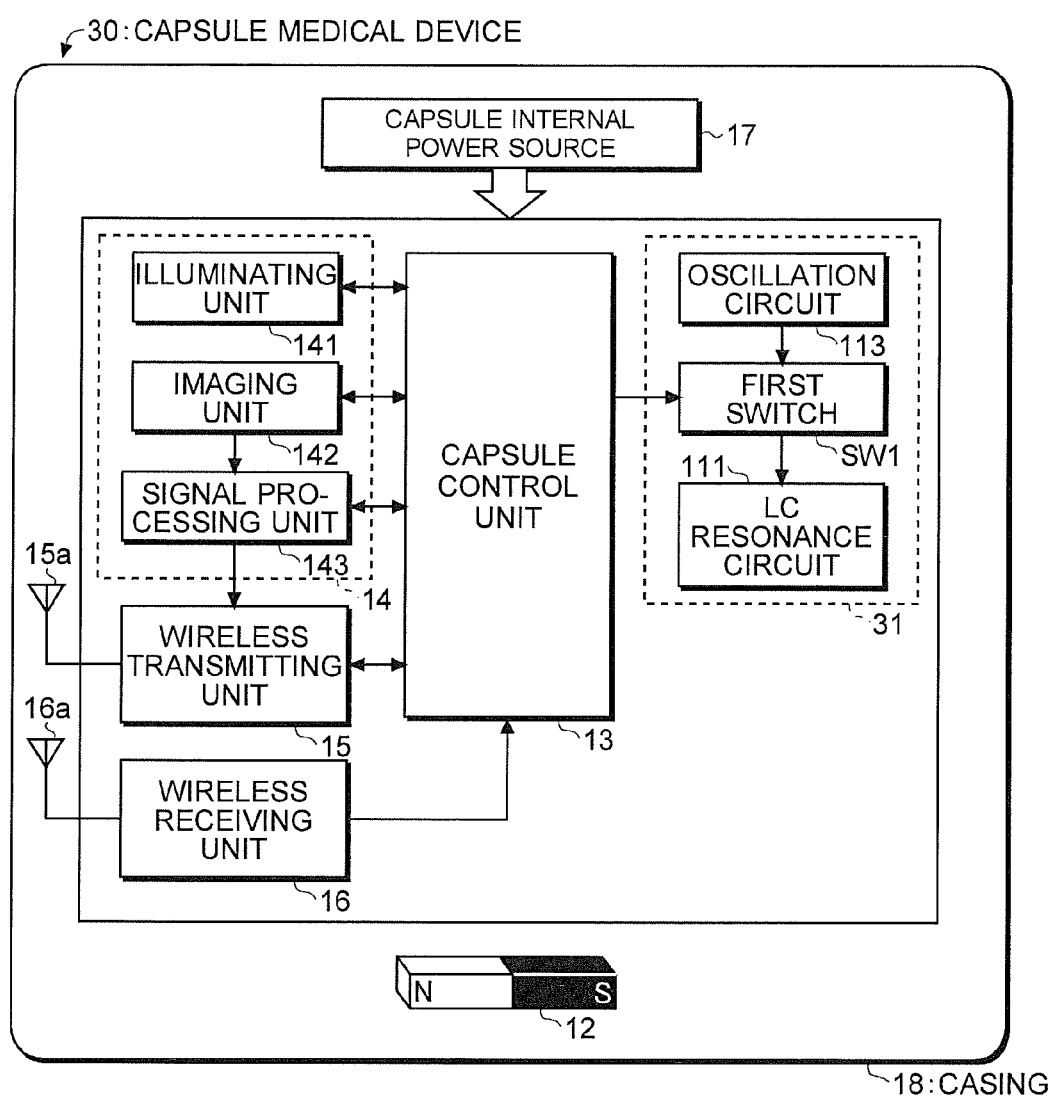
FIG. 16 is a block diagram showing a schematic configuration of a capsule medical device according to a third embodiment of the invention.

As obvious from comparison between FIGS. 16 and 2, in the capsule medical device 30 according to the modification having a configuration similar to that of the capsule medical device 10 according to the first embodiment, the resonance magnetic field generator 11 is replaced with a resonance magnetic field generator 31.

The resonance magnetic field generator 31 has a configuration that the drive circuit 114 in the resonance magnetic field generator 11 is not provided. Instead, the on/off state of the first switch SW1 is directly controlled by the capsule control unit 13.

Since the other configuration is similar to that of the first embodiment of the invention, the detailed description will not be repeated here.

Operation

To the capsule control unit 13, for example, a control signal for switching the operation mode of the capsule medical device 30 is supplied from the external apparatus 200 via the wireless receiving unit 16. That is, the wireless transmitting unit 206 in the external apparatus 200 in the embodiment functions as a control signal transmitting unit that transmits a mode control signal for controlling the on/off state of the first switch SW1 in the capsule medical device 30, and the wireless receiving unit 16 in the capsule medical device 30 functions as a control signal receiving unit that receives a mode control signal.

When the mode control signal is received from the external apparatus 200, according to the mode control signal, the capsule control unit 13 switches the operation mode of the capsule medical device 30 to the active mode or the passive mode. That is, the capsule control unit 13 functions as a first switch control unit for controlling the on/off state of the first switch SW1 on the basis of the mode control signal.

When the operation mode is set to the active mode in accordance with the mode control signal, the capsule control unit 13 turns on the first switch SW1 of a resonance magnetic field generator 31 to supply the guidance signal from the oscillation circuit 113 to the LC resonance circuit 111. On the other hand, when the operation mode is set to the passive mode in accordance with the mode control signal, the capsule control unit 13 turns off the first switch SW1 of a resonance magnetic field generator 31 to electrically interrupt connection between the oscillation circuit 113 and the LC resonance circuit 111. The switching between the active mode and the passive mode in the embodiment may be based on, for example, an operation entered by the operator using the operation unit 203 or the intensity of a detection signal detected by the signal processing unit 211 in the position deriving unit 210.

Figure 17:
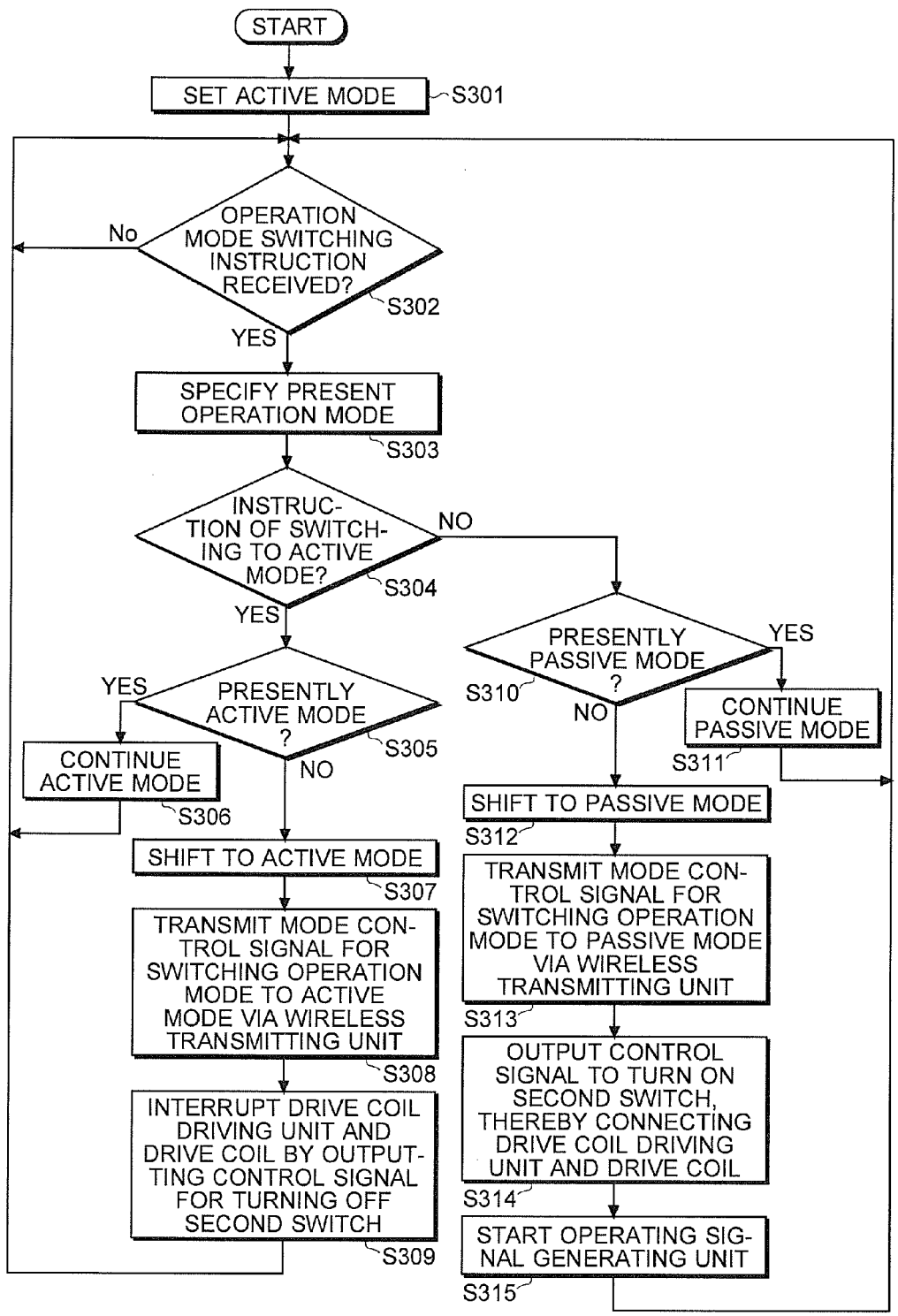
FIG. 17 is a flowchart showing outline of a mode switching process executed by an external apparatus according to the third embodiment of the invention.
Figure 18:
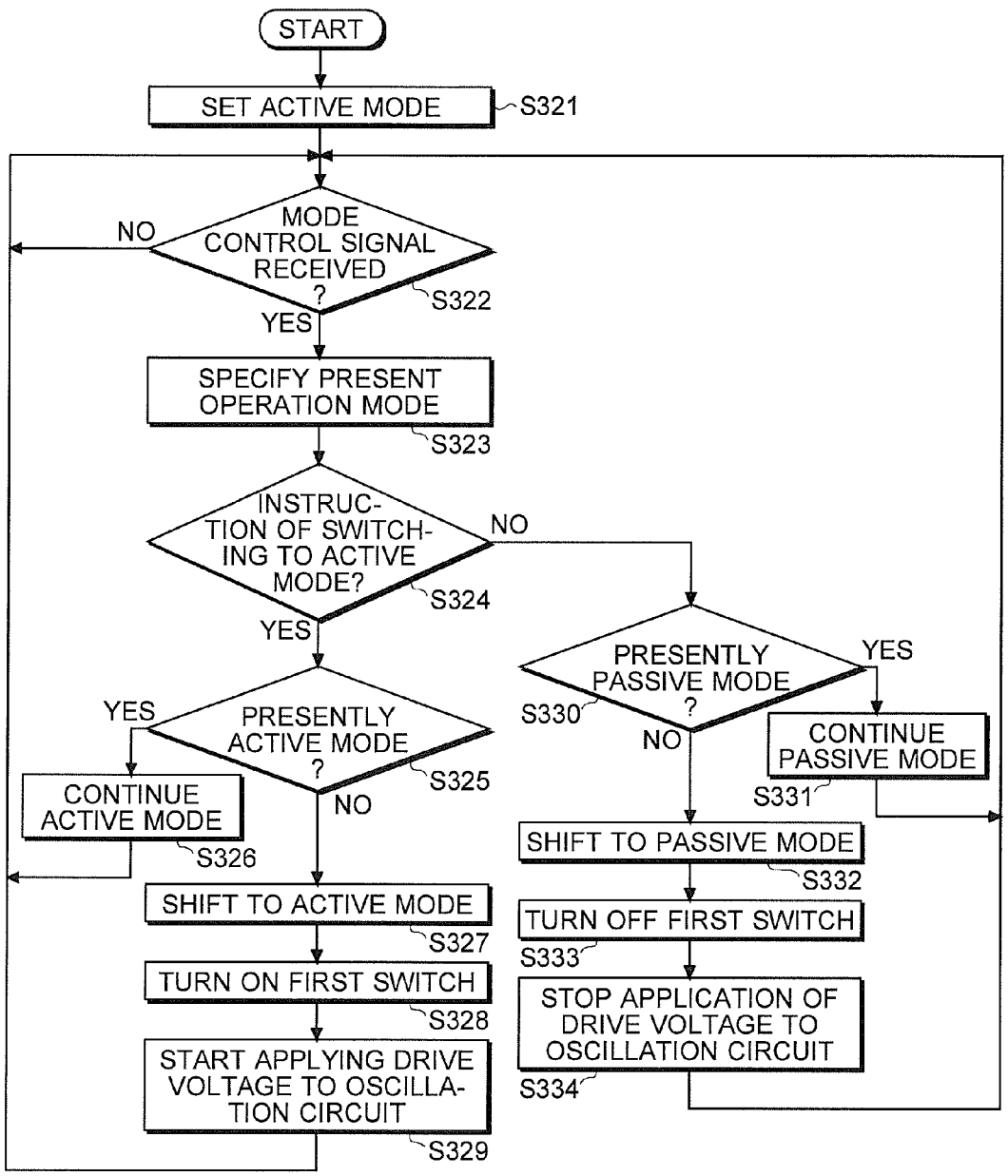
FIG. 18 is a flowchart showing outline of the mode switching process executed by the capsule medical device according to the third embodiment of the invention.

The mode switching process executed by the external apparatus 200 and the mode switching process executed by the capsule medical device 30 in the embodiment will be described in detail with reference to the drawings. FIG. 17 is a flowchart showing outline of the mode switching process executed by the external apparatus 200 in the embodiment. FIG. 18 is a flowchart showing outline of the mode switching process executed by the capsule medical device 30 in the embodiment. In the operation, it is assumed that the operation mode in the beginning of start of the external apparatus 200 and the capsule medical device 30 is the active mode.

Mode Switching Process (External Apparatus)

First, as shown in FIG. 17, when the mode switching process is started, the control unit 201 of the external apparatus 200 sets the active mode (step S301). The details of the step S301 are similar to that of step S101 in FIG. 6 in the first embodiment.

Next, the control unit 201 determines whether the operator enters an operation mode switching instruction from the operation unit 203 (refer to FIG. 1) (step S302), and the control unit 201 waits until the operation mode switching instruction is entered (No in step S302).

When it is determined in step S302 that the operation mode switching instruction is received (Yes in step S302), the control unit 201 specifies the present operation mode by referring to, for example, the memory unit 202 or the like (step S303) and determines whether the switching instruction entered from the operation unit 203 is an instruction of switching to the active mode (step S304).

When it is determined in step S304 that the instruction is the instruction of switching to the active mode (Yes in step S304), the control unit 201 determines whether the present operation mode specified in step S303 is the active mode (step S305). In the case where the present operation mode is the active mode (Yes in step S305), the control unit 201 continues the active mode (step S306) and returns to step S302.

On the other hand, in the case where it is determined in step S305 that the present operation mode is not the active mode (No in step S305), the control unit 201 shifts to the active mode by resetting the operation mode to the active mode (step S307). After that, the control unit 201 transmits the mode control signal for switching the operation mode to the active mode from the wireless transmitting unit 206 to the capsule medical device 30 (step S308), generates the control signal s12 of, for example, the low level which turns off the second switch SW2 and supplies it to the second switch SW2 to turn off a disconnection switch, thereby electrically interrupting the connection of the drive coil driving unit 222 and the drive coils 223a and 223b (step S309) and returning to step S302.

In the case where it is determined in step S304 that the instruction is the instruction of switching to the passive mode (No in step S304), the control unit 201 determines whether the present operation mode specified in step S303 is the passive mode or the like (step S310). In the case where it is the passive mode (Yes in step S310), the control unit 201 continues the passive mode (step S311) and returns to step S302.

On the other hand, in the case where it is determined in step S310 that the present operation mode is not the passive mode (No in step S310), the control unit 201 shifts to the passive mode by resetting the operation mode to the passive mode (step S312). After that, the control unit 201 transmits the mode control signal for switching the operation mode to the passive mode from the wireless transmitting unit 206 to the capsule medical device 30 (step S313). The control unit 201 generates the control signal s12 of, for example, the high level which turns on the second switch SW2 and supplies it to the second switch SW2 to turn on a disconnection switch, thereby electrically connecting the drive coil driving unit 222 and the drive coils 223a and 223b (step S314) and starting the operation of the signal generating unit 221 (step S315). A drive signal having a frequency almost equal to the resonance frequency F0 is output from the signal generating unit 221. The drive signal output from the signal generating unit 221 is current-amplified by the drive coil driving unit 222, and the amplified signal is supplied to the drive coils 223a and 223b via the on-state second switch SW2. In response to the signal, the drive coils 223a and 223b generate the drive magnetic field having a frequency almost equal to the resonance frequency F0 in the detection space K. After step S315, the control unit 201 returns to step S302.

Mode Switching Process (Capsule Medical Device)

As shown in FIG. 18, when the mode switching process is started, the capsule control unit 13 of the capsule medical device 30 sets the active mode (step S321). The mode management can be realized by, for example, like the external apparatus 200, storing a flag for managing a mode in a predetermined storage region in a not-shown memory unit. In the active mode, the capsule control unit 13 generates a control signal of, for example, the low level, supplies the signal to the first switch SW1 to turn off the first switch SW1, thereby electrically disconnecting the oscillation circuit 113 and the LC resonance circuit 111.

Next, the capsule control unit 13 determines whether the mode control signal is received from the external apparatus 200 via the wireless receiving unit 16 (step S322), and waits until the mode control signal is entered (No in step S322).

When it is determined in step S322 that the mode control signal is received (Yes in step S322), the capsule control unit 13 specifies the present operation mode by referring to, for example, a not-shown memory unit or the like (step S323) and determines whether the mode control signal received from the external apparatus 200 is an instruction of switching to the active mode (step S324).

When it is determined in step S324 that the instruction is the instruction of switching to the active mode (Yes in step S324), the capsule control unit 13 determines whether the operation mode specified in step S323 is the active mode (step S325). In the case where it is the active mode (Yes in step S325), the capsule control unit 13 continues the active mode (step S326) and returns to step S322.

On the other hand, in the case where it is determined in step S325 that the present operation mode is not the active mode (No in step S325), the capsule control unit 13 shifts to the active mode by resetting the operation mode to the active mode (step S327). After that, the capsule control unit 13 generates the control signal of, for example, the high level which turns on the first switch SW1 and supplies it to the first switch SW1 to turn on the first switch SW1, thereby electrically connecting the oscillation circuit 113 and the LC resonance circuit 111 (step S328) and starting application of the drive voltage for making the oscillation circuit 113 oscillate at a frequency almost equal to the resonance frequency F0 (step S329). Consequently, the guidance signal having a frequency almost equal to the resonance frequency F0 is output from the oscillation circuit 113 and, by the signal, the LC resonance circuit 111 emits the induced magnetic field into the detection space K. After step S329, the capsule control unit 13 returns to step S322.

In the case where it is determined in step S324 that the instruction is the instruction of switching to the passive mode (No in step S324), the capsule control unit 13 determines whether the present operation mode specified in step S323 is the passive mode or the like (step S330). In the case where it is the passive mode (Yes in step S330), the capsule control unit 13 continues the passive mode (step S331) and returns to step S302.

On the other hand, in the case where it is determined in step S330 that the present operation mode is not the passive mode (No in step S330), the capsule control unit 13 shifts to the passive mode by resetting the operation mode to the passive mode (step S332). After that, the capsule control unit 13 generates the control signal of, for example, the low level which turns off the first switch SW1 and supplies it to the first switch SW1 to turn off the first switch SW1, thereby electrically disconnecting the oscillation circuit 113 and the LC resonance circuit 111 (step S333) and stopping application to the oscillation circuit 113 of the drive voltage for making the oscillation circuit 113 to oscillate (step S334). After that, the capsule control unit 13 returns to step S322.

As described above, according to the embodiment, by switching the first switch SW1 on the basis of the mode control signal transmitted from the external apparatus 200 in the capsule medical device 30 as a body-insertable apparatus, the operation mode can be switched between the active mode in which the LC resonance circuit 111 spontaneously emits the resonance magnetic field and the passive mode in which the LC resonance circuit 111 receives the external magnetic field (drive magnetic field) and emits the resonance magnetic field. By switching the second switch SW2 in accordance with the signal intensity (in other words, intensity of the resonance magnetic field) of the detection signal detected by the sense coil 213 in the external apparatus 200, the operation instruction entered from the operation unit 203, or the like, the operation mode can be switched between the passive mode of making the drive coils 223a and 223b emit the drive magnetic field and the active mode of emitting no drive magnetic field. In such a manner, the position detecting magnetic guidance system capable of detecting the position or the like of the capsule medical device 30 while switching the active and passive modes in accordance with the situation can be realized. Since the other configuration and operation are similar to those of the first or second embodiment (including the modifications) of the invention, the detailed description will not be repeated.

First Modification

The foregoing third embodiment can be modified as follows. In the following, it will be described in detail as a first modification of the third embodiment with reference to the drawings. A position detecting magnetic guidance system of the first modification can use a configuration similar to that of the position detecting magnetic guidance system 1. In the first modification, the capsule medical device 30 is replaced with a capsule medical device 30A shown in FIG. 19.

Configuration

Figure 19:
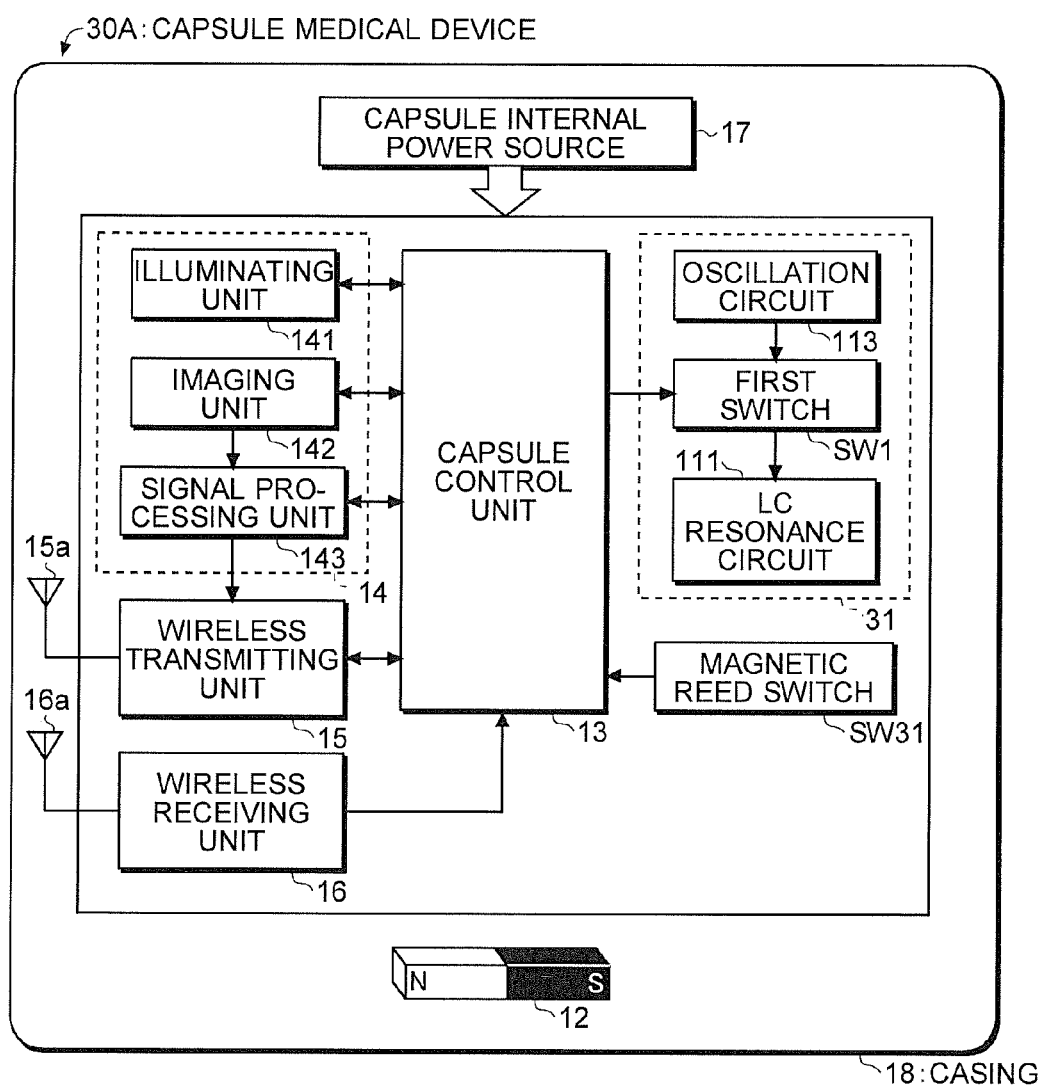
FIG. 19 is a block diagram showing a schematic configuration of a capsule medical device according to a first modification of the third embodiment of the invention.

As obvious from comparison between FIGS. 19 and 16, the capsule medical device 30A of the modification has a configuration similar to that of the capsule medical device 30 according to the third embodiment and is provided with a magnetic reed switch SW31.

When an alternating magnetic field having predetermined intensity or higher (hereinbelow, called mode control magnetic field) is supplied from the outside, the magnetic reed switch SW31 repeats turn-on and turn-off in accordance with the alternating magnetic field. By repeating the turn-on and turn-off, the magnetic reed switch SW31 outputs an alternating signal (hereinbelow, called a mode control signal) which becomes the high level and the low level alternately. The mode control magnetic field is an alternating magnetic field having a frequency which can be responded by the magnetic reed switch SW31 (that is, the magnetic reed switch SW31 can be turned on/off according to the alternation of the magnetic field intensity).

A mode control signal output from the magnetic reed switch SW31 is supplied to the capsule control unit 13. The capsule control unit 13 detects whether the mode control signal is supplied from the magnetic reed switch SW31 and, on the basis of the detection result, switches the operation mode of the capsule medical device 30A between the active mode and the passive mode.

The mode control magnetic field for making the magnetic reed switch SW31 output the mode control signal can be generated by using, for example, the guidance coil 233. As described above, the guidance coil 233 of the first modification and the guidance coil driving unit 232 for driving it also function as a control coil for generating the mode control magnetic field in the detection space K and the control coil driving unit for driving the control coil. The invention, however, is not limited to the configuration. The mode control magnetic field may be generated, for example, by using the drive coils 223a and 223b or by providing a dedicated magnetic field emitter and a dedicated coil.

In the embodiment as described above, the magnetic field is used as a medium of transmitting a mode control signal for switching the operation mode of the capsule medical device 30A, the guidance coil 233 is used as mode control signal transmitting means (the external apparatus 200 side), and a magnetic reed switch is used as mode control signal receiving means (the capsule medical device 30A side).

The mode control magnetic field may have a predetermined pattern. Concretely, the mode control magnetic field may have a predetermined frequency pattern that, for example, oscillation occurs at a first frequency for a first predetermined period and oscillation occurs at a second frequency different from the first frequency for a second predetermined period following the first predetermined period. In such a manner, a configuration that when the pattern is recognized in the capsule control unit 13, the capsule control unit 13 switches the operation mode can be realized, and erroneous operation (erroneous operation mode switching) of the capsule control unit 13 can be prevented. By using the configuration, various information such as a movement instruction and an image capturing instruction in addition to the mode control signal can be transmitted from the external apparatus 200 to the capsule medical device 30A.

As described above, in the modification, by switching the first switch SW1 in accordance with the mode control magnetic field emitted from the external apparatus 200 in the capsule medical device 30A as a body-insertable apparatus, the operation mode can be switched between the active mode in which the LC resonance circuit 111 spontaneously emits the resonance magnetic field and the passive mode in which the LC resonance circuit 111 receives the external magnetic field (drive magnetic field) and emits the resonance magnetic field. By switching the first switch SW1 in accordance with the signal intensity (in other words, intensity of the resonance magnetic field) of the detection signal detected by the sense coil 213 in the external apparatus 200, an operation instruction entered from the operation unit 203, or the like, the operation mode can be switched between the passive mode of making the drive coils 223a and 223b emit the drive magnetic field and the active mode of emitting no drive magnetic field. In such a manner, the position detecting magnetic guidance system capable of detecting the position or the like of the capsule medical device 30A while switching the active and passive modes in accordance with the situation can be realized.

For example, the operation of making the guidance coil 233 generate the mode control magnetic field is similar to that of generating a switching magnetic field in the second embodiment of the invention, so that the detailed description will not be repeated here. The other configuration and operation can be easily reached from the first or second embodiment of the invention (including the modifications) or the third embodiment, so that the detailed description will not be repeated.

The above and other features, advantages and technical and industrial significance of this invention will be better understood by reading the following detailed description of presently preferred embodiments of the invention, when considered in connection with the accompanying drawings.

What is claimed is:

1. A position detecting system comprising:
    a body-insertable apparatus disposed in a state where it is introduced in a subject in a detection space; and
    an external apparatus disposed on the outside of the subject,
    wherein the body-insertable apparatus comprises
        an oscillation circuit that outputs an induction signal of a resonance frequency;
        a resonance circuit that generates a resonance magnetic field having the resonance frequency in accordance with the induction signal output from the oscillation circuit or a drive magnetic field having the resonance frequency generated in the detection space, and is connected between the oscillation circuit and a ground line; and
        a first switch that connects and interrupts the resonance circuit and the oscillation circuit or the ground line,
    the external apparatus comprises
        a drive coil driving unit that outputs a drive signal having the resonance frequency;
        a drive coil that generates the drive magnetic field in the detection space in accordance with the drive signal;
        a second switch that connects and interrupts the drive coil driving unit and the drive coil;
        a magnetic field sensor that detects the resonance magnetic field; and
        a position deriving unit that derives position information of the body-insertable apparatus by using information of the resonance magnetic field detected by the magnetic field sensor,
    the second switch connects the drive coil driving unit and the drive coil when the first switch is in an off state, and disconnects the drive coil driving unit and the drive coil when the first switch is in an on state, and
    the resonance circuit generates the resonance magnetic field in accordance with the induction signal or the drive magnetic field.

2. The position detecting system according to claim 1, wherein
    the external apparatus comprises
        a signal intensity detecting unit that detects signal intensity of a detection signal detected by the magnetic field sensor; and
        a second switch control unit that controls an on/off state of the second switch based on the signal intensity detected by the signal intensity detecting unit.

3. The position detecting system according to claim 1, wherein
    the body-insertable apparatus comprises:

an internal power source that supplies power to the inside of the body-insertable apparatus; and a first switch control unit that controls the first switch in accordance with voltage level of a power source voltage output from the internal power source.

4. The position detecting system according to claim 1, wherein the external apparatus comprises:

a switching coil that generates a switching magnetic field in the detection space; and a switching coil driving unit that supplies a signal for generating the switching magnetic field to the switching coil, and the first switch is a magnetic reed switch which is turned on/off according to the switching magnetic field.

5. The position detecting system according to claim 1, wherein the external apparatus comprises a control signal transmitting unit that transmits a control signal for controlling an on/off state of the first switch to the body-insertable apparatus, and the body-insertable apparatus comprises:

a control signal receiving unit that receives the control signal; and a first switch control unit that controls an on/off state of the first switch based on the switch signal.

6. The position detecting system according to claim 5, wherein the control signal transmitting unit comprises a control coil that forms a control magnetic field in the detection space; and a control coil driving unit that supplies a signal for generating the control magnetic field to the control coil, and the control signal receiving unit comprises a magnetic reed switch that is turned on/off according to the control magnetic field; and a first switch control unit that controls the on/off state of the first switch based on a signal output from the magnetic reed switch.

7. The position detecting system according to claim 6, wherein the control coil driving unit supplies a signal for generating the control magnetic field in a predetermined pattern to the control coil.

8. The position detecting system according to claim 1, wherein the body-insertable apparatus comprises a magnetic field generating unit that generates a magnetic field, and the external apparatus comprises a guidance coil that forms a guidance magnetic field which acts on the magnetic field generating unit in the detection space; and a guidance coil driving unit that supplies a signal for generating the guidance magnetic field to the guidance coil.

9. The position detecting system according to claim 4, wherein the body-insertable apparatus comprises a magnetic field generating unit that generates a magnetic field, the external apparatus comprises a guidance coil that forms a guidance magnetic field which acts on the magnetic field generating unit in the detection space; and a guidance coil driving unit that supplies a signal for generating the guidance magnetic field to the guidance coil, and the guidance coil or the drive coil is used as the switching coil.

10. The position detecting system according to claim 6, wherein the body-insertable apparatus comprises a magnetic field generating unit that generates a magnetic field, the external apparatus comprises a guidance coil that forms a guidance magnetic field which acts on the magnetic field generating unit in the detection space; and a guidance coil driving unit that supplies a signal for generating the guidance magnetic field to the guidance coil, and the guidance coil or the drive coil is used as the control coil.

11. The position detecting system according to claim 1, wherein the external apparatus comprises an averaging unit that averages the position information.

12. The position detecting system according to claim 11, wherein the averaging unit changes a parameter of position information to be averaged, between an on state and an off state of the second switch.

13. The position detecting system according to claim 1, wherein the external apparatus comprises an averaging unit that averages information of the resonance magnetic field.

14. The position detecting system according to claim 13, wherein the averaging unit sets different parameters of information of the resonance magnetic field to be averaged for the case where the second switch is in the on state and the case where the second switch is in the off state.

15. The position detecting system according to claim 1, wherein the position deriving unit derives the position information of the body-insertable apparatus from information obtained by eliminating the information of the drive magnetic field from the magnetic field information included in a detection signal detected by the magnetic field sensor.

16. The position detecting system according to claim 1, wherein the position deriving unit derives the position information of the body-insertable apparatus from information obtained by eliminating information of unnecessary magnetic field generated when the drive coil is excited by the resonance magnetic field from the magnetic field information included in a detection signal detected by the magnetic field sensor in a state where the second switch is in an on state.

17. The position detecting system according to claim 1, wherein the body-insertable apparatus comprises an imaging unit that images the inside of the subject to capture an image; and an image transmitting unit that transmits the image captured by the imaging unit to the external apparatus, and the external apparatus comprises an image receiving unit that receives the image transmitted from the image transmitting unit; and a display unit that displays the image received by the image receiving unit together with the position information.

18. A method for operating a position detecting system that detects a position in a subject of a body-insertable apparatus including a resonance circuit that generates a resonance magnetic field spontaneously or being induced by an external magnetic field, the position detecting method comprising:

a resonance magnetic field intensity detecting step of detecting, by a sense coil, intensity of the resonance magnetic field;

a resonance magnetic field intensity determining step of determining, by a control unit, whether the magnetic field intensity detected at the resonance magnetic field intensity detecting step is equal to or larger than a predetermined value;

an external magnetic field generating step, when the magnetic field intensity is smaller than the predetermined value, of generating, by a drive coil and a drive coil driving unit, the external magnetic field;

a resonance magnetic field detecting step of detecting, by a sense coil, a resonance magnetic field spontaneously generated by the resonance circuit or a resonance magnetic field generated by being induced by the external magnetic field generated at the external magnetic field generating step; and a position deriving step of deriving, by a position deriving unit, position information indicative of a position in the subject of the body-insertable apparatus based on the resonance magnetic field detected at the resonance magnetic field detecting step.

19. The method according to claim 18, wherein the position deriving step includes a position information storing step of storing, by the control unit, the position information derived in the position deriving step by an amount of predetermined number of times; and a position information averaging step of averaging, by the control unit, the position information of the amount of the predetermined number of times stored in the position information storing step, and the position information indicative of the position in the subject of the body-insertable apparatus is derived based on the averaged position information by the position deriving unit.

* * * * *